(12) United States Patent
Malmqvist et al.

(10) Patent No.: US 8,021,626 B2
(45) Date of Patent: *Sep. 20, 2011

(54) METHOD AND DEVICE FOR LAMINAR FLOW ON A SENSING SURFACE

(75) Inventors: Magnus Malmqvist, Uppsala (SE); Hakan Roos, Uppsala (SE); Stefan Sjolander, Uppsala (SE); Mattias Tidare, Uppsala (SE); Hakan Sjodin, Knivsta (SE); Ralph Stalberg, Telemark (NO)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,221

(22) Filed: Apr. 26, 2010

(65) Prior Publication Data

US 2010/0260642 A1 Oct. 14, 2010

Related U.S. Application Data

(63) Continuation of application No. 12/494,930, filed on Jun. 30, 2009, now Pat. No. 7,736,587, which is a continuation of application No. 11/295,161, filed on Dec. 6, 2005, now Pat. No. 7,582,487, which is a continuation of application No. 09/760,213, filed on Jan. 12, 2001, now Pat. No. 7,105,356, which is a continuation of application No. 09/009,139, filed on Jan. 20, 1998, now Pat. No. 6,200,814.

(51) Int. Cl.
*G01N 21/17* (2006.01)

(52) U.S. Cl. ........ 422/417; 422/401; 422/403; 422/404; 422/504; 422/82.05; 435/283.1; 73/64.54; 356/246

(58) Field of Classification Search ............... 422/82.05, 422/57, 58, 68.1, 400–417; 436/165, 180; 356/246, 440; 435/283.1; 73/64.54
See application file for complete search history.

(56) References Cited

U.S. PATENT DOCUMENTS

| | | | |
|---|---|---|---|
| 4,022,575 A | 5/1977 | Hansen et al. | |
| 4,056,324 A | 11/1977 | Gohde | |
| 4,997,278 A | 3/1991 | Finlan et al. | |
| 5,313,264 A | 5/1994 | Ivarsson et al. | |
| 5,485,277 A * | 1/1996 | Foster | 356/445 |
| 5,773,298 A | 6/1998 | Lynggaard et al. | |
| 6,200,814 B1 | 3/2001 | Malmqvist et al. | |
| 6,289,144 B1 * | 9/2001 | Neuschafer et al. | 385/12 |

FOREIGN PATENT DOCUMENTS

| | | |
|---|---|---|
| EP | 0 286 195 | 10/1988 |
| EP | 0 469 377 | 7/1991 |
| WO | WO 90/05305 | * 5/1990 |
| WO | WO 93/24231 | 12/1993 |
| WO | WO 94/27137 | 11/1994 |
| WO | WO 96/10178 | 4/1996 |
| WO | WO 96/35940 | * 11/1996 |
| WO | WO 97/01087 | 1/1997 |

* cited by examiner

*Primary Examiner* — In Suk Bullock
*Assistant Examiner* — Timothy G Kingan

(57) ABSTRACT

Methods and devices are provided for controlling a fluid flow over a sensing surface within a flow cell. The methods employ laminar flow techniques to position a fluid flow over one or more discrete sensing areas on the sensing surface of the flow cell. Such methods permit selective sensitization of the discrete sensing areas, and provide selective contact of the discrete sensing areas with a sample fluid flow. Immobilization of a ligand upon the discrete sensing area, followed by selective contact with an analyte contained within the sample fluid flow, allows analysis by a wide variety of techniques. Sensitized sensing surfaces, and sensor devices and systems are also provided.

11 Claims, 23 Drawing Sheets

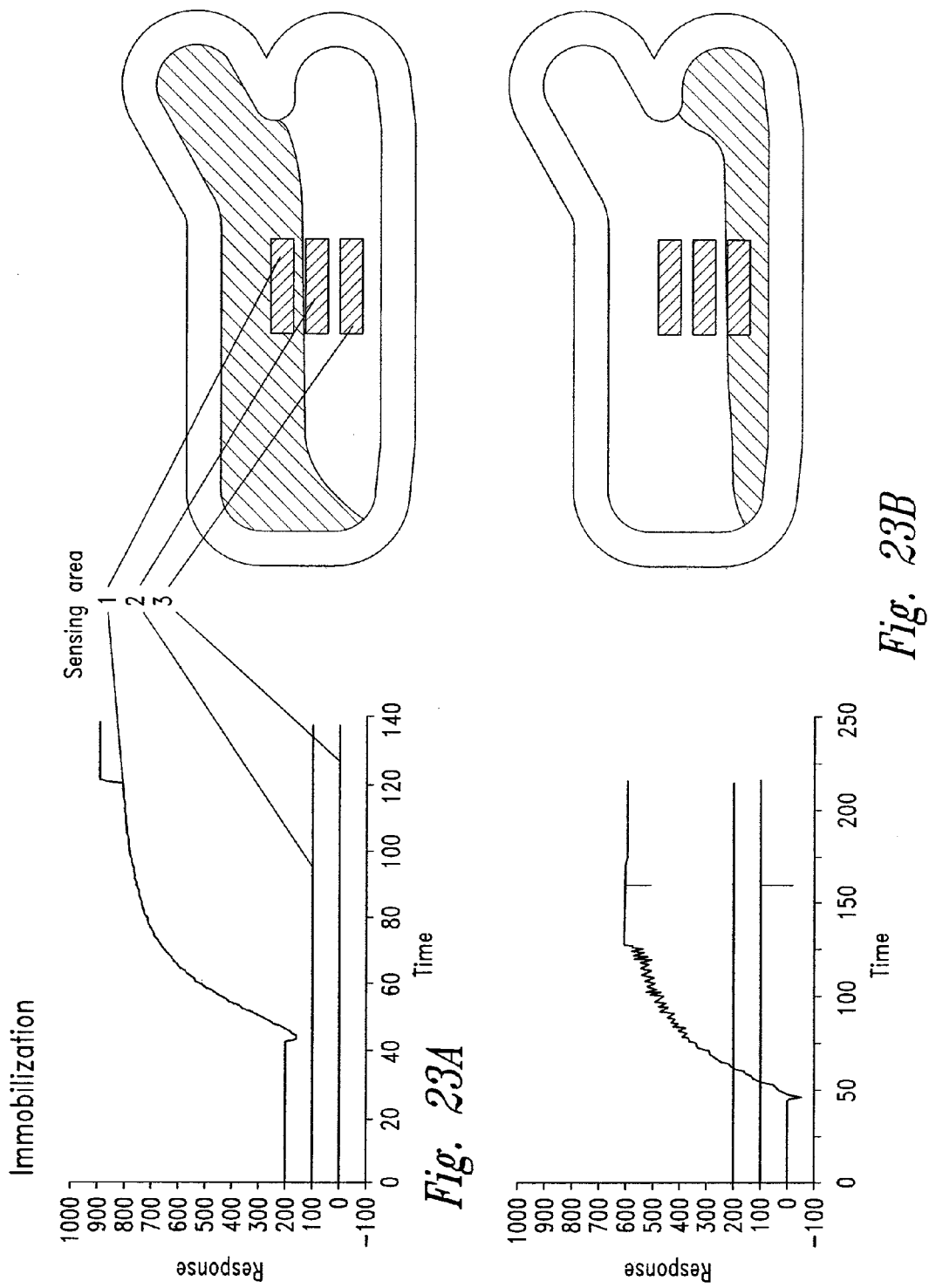

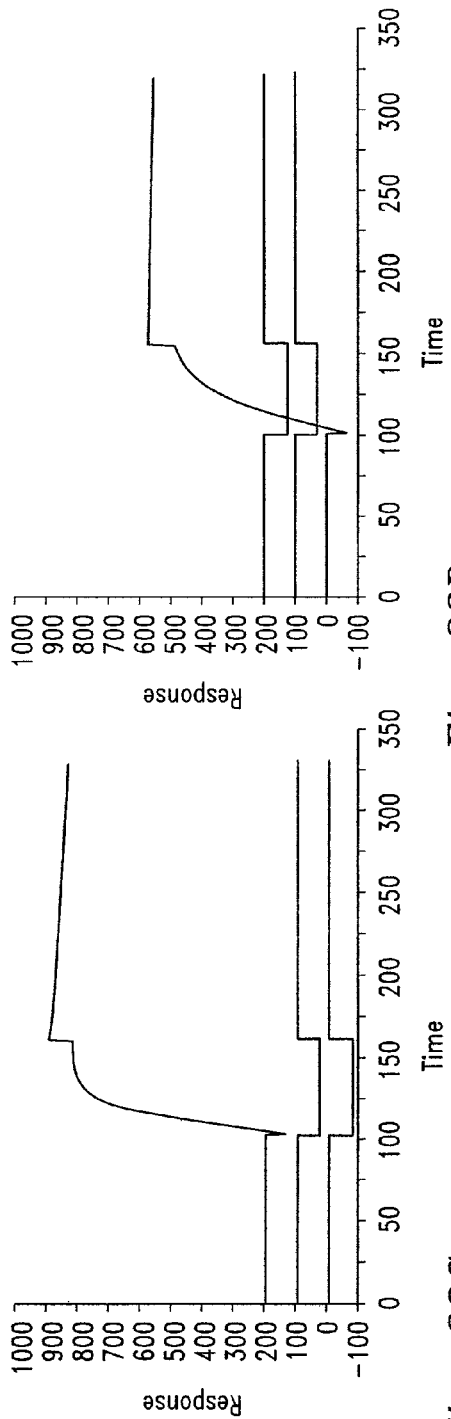
Fig. 23C
Fig. 23E
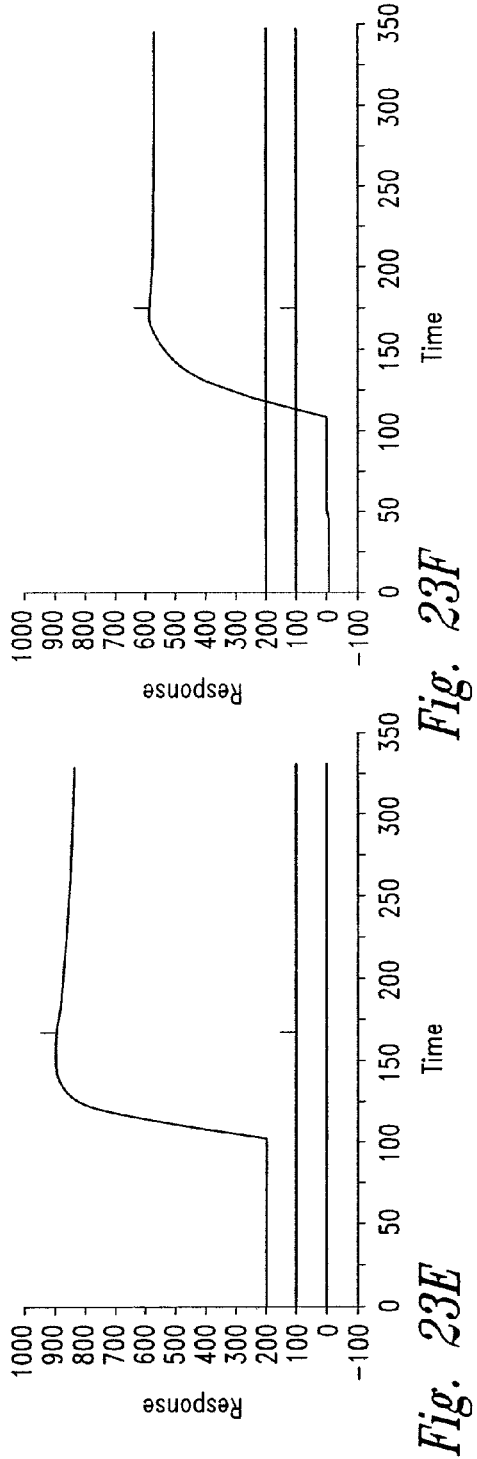
Fig. 23D
Fig. 23F

METHOD AND DEVICE FOR LAMINAR FLOW ON A SENSING SURFACE

CROSS-REFERENCE TO RELATED APPLICATIONS

This application is a continuation of U.S. patent application Ser. No. 12/494,930 filed Jun. 30, 2009 (U.S. Pat. No. 7,736,587), which is a continuation of Ser. No. 11/295,161, filed Dec. 6, 2005 (U.S. Pat. No. 7,582,487); which is a continuation of U.S. patent application Ser. No. 09/760,213, filed Jan. 12, 2001 (U.S. Pat. No. 7,105,356); which is a continuation of U.S. patent application Ser. No. 09/009,139, filed Jan. 20, 1998 (U.S. Pat. No. 6,200,814).

FIELD OF INVENTION

The present invention generally relates to the control of a fluid flow over a sensing surface within a flow cell and, more specifically, to the use of laminar flow techniques to position a fluid flow over one or more discrete sensing areas within a flow cell, as well as the use thereof in the preparation of sensing surfaces and in analytical methods, devices and systems related thereto.

BACKGROUND OF INVENTION

Instrumentation for real-time Biomolecular Interaction Analysis (BIA) is commercially available from Biacore AB (Uppsala, Sweden) under the trade name BIAcore (hereinafter "the BIAcore instrument"). The BIAcore instrument employs surface plasmon resonance (SPR) to investigate interactions between molecules at the surface of a sensor chip, and includes a processing unit with liquid handling and optical systems, a sensor chip, and a computer for control and data evaluation. One molecule, referred to as the "ligand," is immobilized on the surface of the sensor chip, and the other molecule, the "analyte," flows over the surface of the sensor chip. As the analyte interacts with the immobilized ligand, SPR is used to measure a change in refractive index on the surface of the sensor chip. Selective interactions of the analyte to the immobilized ligand gives this technique specificity, and also enables analysis of interactions in complex mixtures.

The BIAcore instrument has been used extensively, and a large volume of literature has been published concerning its operation and applicability. For example, published PCT WO 90/05295 discloses in greater detail the construction and operation of the BIAcore instrument, while published PCT applications WO 90/05303 and WO 90/05305 are directed to various sensor surfaces for use therewith. Further, the BIAtechnology, BIAapplication, and BIAcore Handbooks published by BIAcore AB describe in considerable detail the operation and construction of the BIAcore instrument.

In general, an analyte present within a liquid sample interacts with the ligand associated with, for example, a dextran matrix bound to the surface of the sensor chip. Binding of the analyte by the ligand gives rise to an increase in refractive index which is monitored in real time by a change in the resonance angle as measured by SPR. The data take the form of a sensorgram which plots the signal in resonance units (RU) as a function of time. A signal of 1,000 RU corresponds to the binding of about 1 ng of analyte per mm$^2$ (Johnsson et al., *Anal. Biochem.* 198:268-277, 1991; Fagerstam et al., *J. Chromatography* 597:397-410, 1992; Stenberg et al., *Colloid and Interface Science* 143:513-526, 1991).

During operation of the BIAcore instrument, the sample is delivered to the sensor chip utilizing an integrated microfluidic cartridge (IFC). The IFC consists of a series of precision-cast channels in a hard silicon polymer plate, forming sample loops and flow channels for buffer and sample delivery. The IFC is pressed into contact with the sensor chip by a docking mechanism within the BIAcore instrument. A representative IFC as used by the BIAcore instrument is depicted in FIG. 1A, which illustrates the channels and valves (as viewed from above), with the inset showing a side view of the same and depicting a flow cell formed from pressing the IFC against the sensor chip.

Sample flow through the IFC is controlled by a set of pneumatically actuated diaphragm valves which direct the sample through the various channels to the sensing surface of the sensor chip. In this manner, the BIAcore instrument (e.g., BIAcore 2000) permits single or multichannel analysis in up to four flow cells. For example, FIG. 1B illustrates sample being passed through three flow cells in series (labeled FC 1, FC 2 and FC 3). Although not specifically depicted in FIG. 1B, sample can also pass through just a single flow cell for analysis (e.g., FC 1).

Existing BIAcore instruments employ flow cells having a cross sectional area of 0.05×0.5 mm and a length of 2.4 mm, giving a volume of about 60 nanoliters (nl), and having a total sensing surface area in each flow cell of approximately 1.2 mm$^2$. A focused incident light illuminates approximately 1.6 mm of the length of the sensing surface for each flow cell, with the detector imaging about 0.17 mm of the width of the sensing surface. This corresponds to a sensing area within each flow cell of about 0.3 mm$^2$. Each flow cell in the BIAcore instrument contains a single sensing area. Thus, if the sample is to contact four different sensing areas, passage of the sample through four separate flow cells is required (i.e., FC 1, FC 2, FC 3 and FC 4).

While sample delivery to multiple flow cells as presently employed in the BIAcore instrument offers numerous advantages, and represents the state of the art with respect to sample delivery techniques, improvements thereto are still desired. For example, in the context of kinetic measurements, it is important that sample be delivered to each flow cell in a well-defined volume or "plug," with minimal dispersion at sample-buffer boundaries. Such a sample plug is created by switching between sample and buffer flow in the IFC with aid of the pneumatic valves. While dispersion is minimized by keeping dead volumes between the valves and flow cells small, there are still periods at the start and end of sample introduction where the concentration of the sample is diluted by dispersion (i.e., mixing of the sample with the running buffer in the system). Further, dispersion increases with the number of flow cells in series (as depicted in FIG. 1B). Such dispersion results in a time lag in both the rise and fall of the sensorgram at the beginning and end of sample introduction. These so-called "rise and fall times" limit the ability to resolve fast reaction kinetics (i.e., interactions with high rate constants). One way to solve this limitation is to increase the flow rate. Unfortunately, increasing the flow rate means increased sample consumption. There are also practical and design limitations in terms of, for example, liquid pressure which provide an upper limit for the flow rate.

In addition, temperature variations between flow cells can negatively impact sample analysis. Since refractive index, reaction kinetics and mass transport of the analyte to the sensing surface are all sensitive to temperature, it is important that such measurements be carried out at controlled temperatures. Due to physical separation of the flow cells, and hence the sensing surfaces, temperature fluctuations between flow cells can be a source of measurement error. Further, the flow cells depicted in FIGS. 1A and 1B do not permit controlled sample delivery to discrete areas within a single flow cell, nor do they allow immobilization of different ligands to discrete sensing areas within a single flow cell. Rather, such modifications are only achieved within separate flow cells, and thus are accompanied by the limitations as noted above.

Accordingly, there is a need in the art for improved sample delivery techniques within the context of flow cell-based detection instruments, such as the BIAcore instrument, as well as for other instruments of similar design or operation. To that end, any instrument which detects a measurable change in a property associated with a flow cell-based sensing structure may benefit from improved sample delivery techniques. Such improvements should provide fast liquid exchange rates between sample and buffer, maintain constant temperature control across multiple sensing areas, and permit a variety of sample delivery techniques to multiple sensing areas within the flow cell.

The present invention fulfills these needs and provides further related advantages.

SUMMARY OF THE INVENTION

In brief, the present invention is directed to the control of a fluid flow over a sensing surface within a flow cell and, more specifically, to the use of laminar flow techniques to position the fluid flow over one or more discrete sensing areas within the flow cell More specifically, by varying the individual flow rates of at least two laminar fluid flows, an interface between the two flows may be laterally moved over the sensing surface within the flow cell. In this manner, the flows may be controllably positioned within the flow cell over one or more discrete sensing areas, and further permits a wide range of surface modification and/or interaction at the discrete sensing areas.

One aspect of the invention provides a method of sensitizing a sensing surface arranged to be passed by a liquid flow. The term "sensitizing" means any process or activation of the sensing surface that results in the surface being capable of specifically interacting with a desired analyte. This method comprises providing a laminar flow of a first fluid and a laminar flow of a second fluid adjacent to the flow of the first fluid so that the two laminar flows together pass over the sensing surface with an interface to each other, with at least the first fluid being capable of sensitizing the sensing surface, and adjusting the relative flow rates of one or both of the two laminar flows to position the interface between the flows so that each laminar flow contacts a defined area of the sensing surface for selective sensitization thereof.

In one embodiment, the sensing surface is sensitized by contacting the surface with a first fluid that sensitizes the same, and a second fluid that does not sensitize the surface. In a variant of this embodiment, the procedure is repeated such that the first fluid is replaced by a fluid that does not sensitize the sensing surface, and the second fluid is replaced by a fluid capable of sensitizing the sensing surface differently than the first fluid to produce two differently sensitized areas, optionally spaced apart by, or adjacent to, a non-sensitized area of the sensing surface. In other embodiments, a stepwise gradient may be produced by varying the relative flow rates of the laminar flows to displace the interface laterally and provide a gradient-sensitized area on the sensing surface or, alternatively, by continuously varying the relative flow rates of the laminar flows to generate a continuous gradient-sensitized area.

In still another embodiment, an additional laminar flow of a third fluid is provided on the other side of the flow of the first fluid so that the laminar flow of the first fluid is sandwiched between the laminar flows of the second and third fluids. This permits the flow of the first fluid to be positioned laterally on the sensing surface. If the second and third fluids, which may be the same or different liquids, are not capable of sensitizing the sensing surface, a streak or row of sensitizing fluid may be controllably positioned on the sensing surface. By successively repeating the above procedure with at least one different sensitizing first fluid, and with varied relative flow rates of the second and third fluids, two or more rows of sensitized surface areas may be provided on the sensing surface.

In yet another embodiment, the method is used to produce either a row or matrix of sensitized areas on the sensing surface. This may be achieved by repeating the procedure with a different sensitizing fluid or fluids and applying the laminar flows at an angle, typically transversely, to the original flow direction. Such rows or matrixes have a number of beneficial applications as described in more detail below.

Another aspect of the invention provides a method of analyzing a fluid sample for one or more analytes. This method comprises sensitizing a sensing surface by immobilization of an analyte-specific ligand on the sensing surface by the methods described herein, contacting the sensing surface with the fluid sample, and detecting interaction of analyte in the fluid sample with the sensitized area or areas of the sensing surface. One or more non-sensitized areas may be used as a reference area or areas or, alternatively, one or more areas sensitized with a control ligand may be employed.

Still another aspect of the invention provides a method of analyzing a fluid sample for an analyte where laminar flow of the fluid is to position the sample flow on the desired sensitized area or areas. The method comprises providing a sensitized area on the sensing surface of a flow cell, the sensitized area being capable of selectively interacting with the analyte; passing a first laminar flow of the fluid sample over the sensing surface, but not in contact with the sensitized area; passing a second laminar flow of fluid that is not capable of interacting with the sensitized area over the sensing surface, the second laminar flow being adjacent to the first laminar flow and forming an interface therewith; adjusting the relative flow rates of the first and/or second laminar flows such that the first laminar flow of fluid sample passes over the sensitized area; and detecting interaction of analyte in the fluid sample upon contact with the sensitized area.

Another aspect of the invention provides a method of analyzing a fluid sample for an analyte, where the whole sensing surface is sensitized and only a part of the sensitized surface is contacted with the sample flow, whereas the other part is used as a reference area. In this way, bleeding as well as other uncontrollable events on the sensing surface may be referenced away. This method comprises providing a sensitized surface which is capable of selectively interacting with the analyte; passing a first laminar flow of the fluid sample over a first part of the sensitized surface (i.e., a first sensing area); simultaneously passing a second laminar flow of fluid that is not capable of interacting with the sensitized surface over the remainder of the sensitized surface (i.e., a second sensing area), wherein the second laminar flow is adjacent to the first laminar flow and the second sensing area serves as a reference area; and detecting interaction of analyte in the fluid sample with the first sensing area. In a further embodiment, the relative flow rates of the first and/or second laminar flows are adjusted such that the first laminar flow passes over at least a portion of the second sensing area, and interaction of analyte in the sample flow is detected with this newly contacted portion of the second sensing area.

Yet other aspects of the invention provide methods of studying the association or dissociation of an analyte to or from a sensing surface, where laminar flow techniques are used to rapidly shift a sample fluid flow laterally in a flow cell to a position where the sample flow contacts a sensitized sensing area. The method for studying association comprises providing a flow cell having a sensitized sensing area on a sensing surface thereof which is capable of interacting with the analyte; passing fluid sample in a first laminar flow through the flow cell; passing analyte-free fluid in a second laminar flow through the flow cell, the second laminar flow being adjacent to the first laminar flow and forming an interface therewith; setting the relative flow rates of the fluid flows to place the interface between the laminar flows so that the sample fluid flow does not contact the sensitized sensing area; changing the relative flow rates of the laminar flows to displace the interface laterally so that the sample flow contacts the sensitized sensing area; and determining association of analyte to the sensitized sensing area. Similarly, the method for studying dissociation comprises shifting the sample flow laterally so that the sample flow is no longer in contact with the sensitized sensing area; and determining dissociation of analyte from the sensitized sensing area.

Still another aspect of the invention provides a sensor device comprising a flow cell having an inlet end and an outlet end; at least one sensing surface on a wall surface within the flow cell located between the inlet and outlet ends; wherein the flow cell has at least two inlet openings at the inlet end, and at least one outlet opening at the outlet end, such that separate laminar fluid flows entering the flow cell through the respective inlet openings can flow side by side through the flow cell and contact the sensing surface. In one embodiment of the sensor device, the flow cell has two inlet openings and at least one outlet opening, and is of the Y flow cell type (i.e., having two inlets and a single outlet). In another embodiment, the flow cell has three inlet openings and at least one outlet opening to establish three laminar fluid flows in a sandwich fashion through the flow cell, and is of the flow cell type (i.e., having three inlets and a single outlet).

In still another embodiment, the flow cell is of the two-dimensional type. One variant of such a two-dimensional flow cell has at least two first inlets and at least one first outlet, and in an angular relationship to the fluid pathway between them (usually transversely), at least two second inlets, and at least one second outlet. A representative flow cell of this type is a two-dimensional Ψ cell. Another variant of a two-dimensional flow cell has the sensing surface turnably mounted within the flow cell to permit it to be passed by fluid flows in two dimensions. The sensing surface may have at least two adjacent sensing areas in the flow direction of the flow cell, particularly at least one sensing area and at least one reference area. Preferably, at least one sensing area is capable of specifically interacting with an analyte.

Yet another aspect of the invention provides a sensor system, comprising a flow cell having an inlet end and an outlet end; at least one sensing area on a sensing surface within the flow cell between the inlet and outlet ends; the flow cell having at least two inlet openings at the inlet end, and at least one outlet opening at the outlet end; means for applying laminar fluid flows through the inlet opening such that the laminar fluid flows pass side by side through the flow cell over the sensing surface; means for varying the relative flow rates of the laminar flows of fluids to vary the respective lateral extensions of the laminar flows over the sensing surface containing the sensing area or areas; and, detection means for detecting interaction events at the sensing area or areas.

These and other aspects of this invention will be evident upon reference to the attached drawings and the following detailed description. Furthermore, certain references have been cited herein for the purpose of clarity and completeness. Such references are each incorporated herein by reference in their entirety.

BRIEF DESCRIPTION OF THE DRAWINGS

FIG. 3A illustrates the sample interface positioned adjacent the sensing area, while

FIG. 4A illustrates a Y flow cell having two sensing areas with the sample flow initially adjacent to both sensing areas, while

FIG. 7A depicts the concentration of the sample at different contact times in a cross section of the Y flow cell, while

FIGS. 23A through 23F illustrates sensitization at two discrete sensing areas, and selective analysis of analytes specific to such discrete sensing areas.

DETAILED DESCRIPTION OF THE INVENTION

Figure 1A:
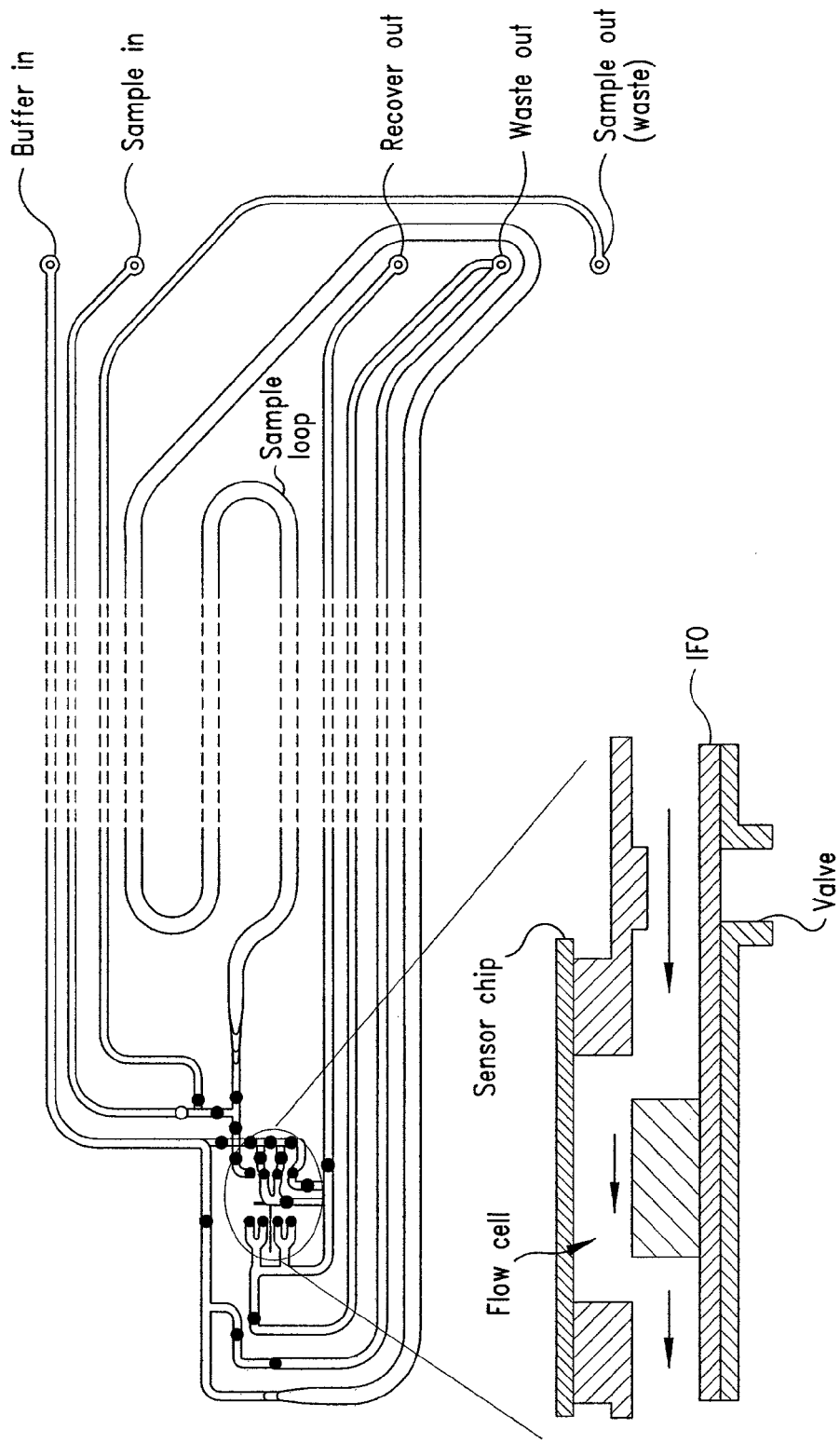
FIG. 1A (prior art) depicts the channels and valves in an IFC as viewed from above, while the insert shows a side view of how the flow cells are formed by pressing the sensor chip against the IFC.
Figure 1B:
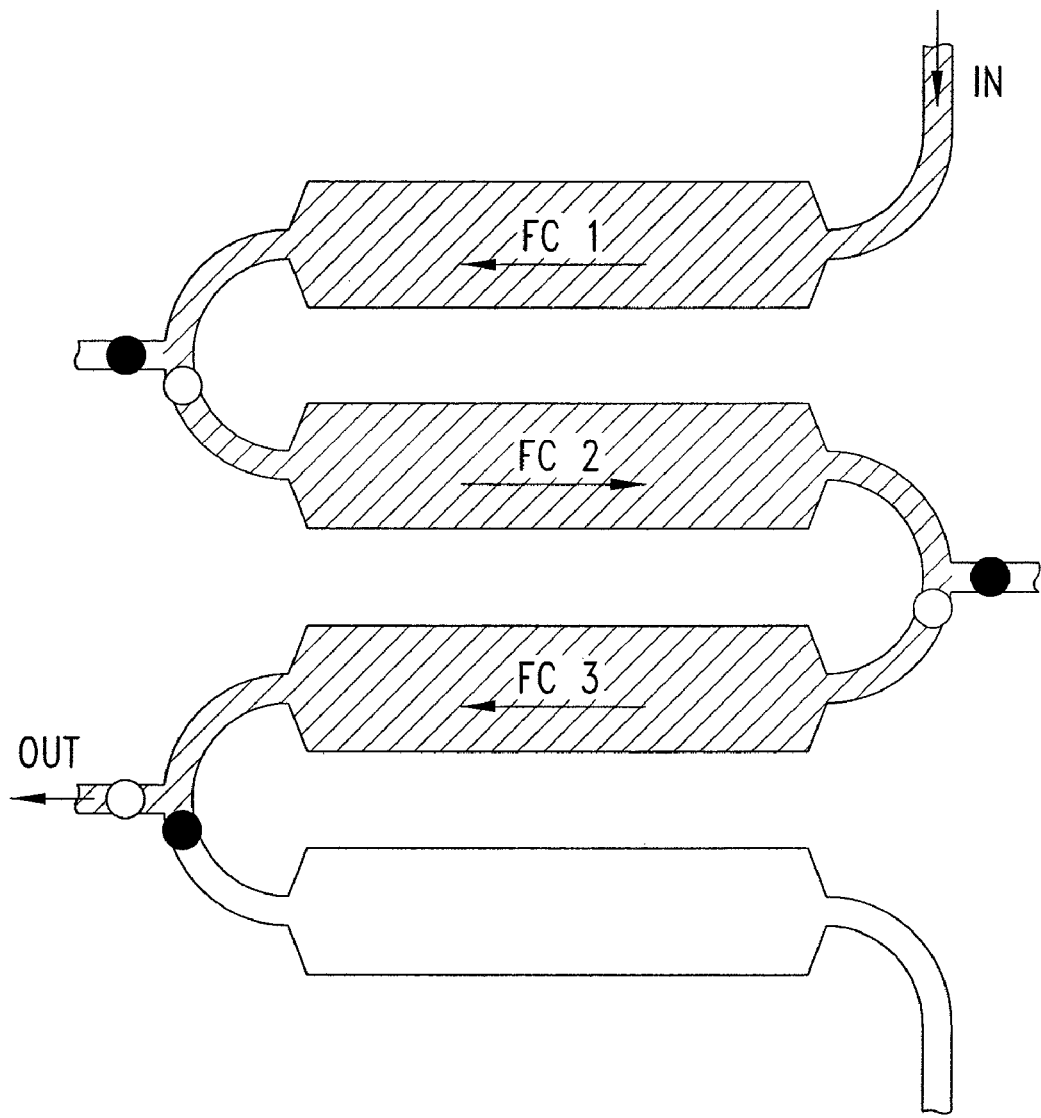
FIG. 1B (prior art) illustrates sample flow through three of four flow cells (the empty and filled circles represent open and closed valves, respectively).

As mentioned above, this invention is generally directed to the control of a fluid flow over a sensing surface using laminar flow techniques to bring the fluid (also referred to herein as "sample flow" or "sample") into contact with one or more discrete areas on the sensing surface (called "sensing areas"), as well as to the preparation of sensing surfaces and in analytical methods, devices and systems related thereto. In the context of preparing a sensing surface, a ligand may be associated with a discrete sensing area on the sensing surface (referred to herein as "sensitization") by selectively contacting the discrete sensing area of the sensing surface with a sample containing the ligand under laminar flow conditions within a flow cell. The configuration and dimensions of the flow cells of this invention may vary widely depending upon the specific application and/or detection method.

To this end, representative detection methods include, but are not limited to, mass detection methods, such as piezoelectric, optical, thermo optical and surface acoustic wave (SAW) methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging, such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers. While the present invention is hereinafter illustrated in the context of SPR spectroscopy, it should be understood that the invention is not limited in this manner. Rather, any instrumentation or technique wherein a sample is brought into contact with a sensing surface within a flow cell under laminar flow conditions may benefit from this invention.

As mentioned above, the present invention involves contacting a sample with one or more discrete sensing areas on a sensing surface under laminar flow conditions within a flow cell. As used herein, the term "laminar flow" corresponds to a Reynolds number below 2000, and preferably below 20. The Reynolds number ($R_e$) is used to describe the character of a liquid flow over the sensing surface, and may be expressed by the following Equation (1):

$$R_e = \frac{Vd\rho}{\mu} \quad (1)$$

where V is the average linear flow rate (m/s), d is the diameter of the "pipe" (m), $\rho$ is the density of the fluid (kg/m$^3$) and $\mu$ is the absolute viscosity of the fluid (Ns/m$^2$). In the context of a flow cell having a rectangular cross section, the pipe diameter is more appropriately replaced with the hydraulic diameter ($D_h$), which is given by four times the cross sectional area divided by the perimeter of the flow cell (i.e., $D_h$=2wh/(w+h) where w and h are the width and height, respectively, of the flow cell). Thus, the Reynolds number of a flow cell having a rectangular cross section may more accurately be represented by Equation (2):

$$R_e = \frac{VD_h\rho}{\mu} \quad (2)$$

It should be noted that Equation (2) assumes that the sensing surface is ideally smooth and with a curvature that can be neglected. Thus, any irregularities, pronounced curvature of the surface or sharp bends within the flow cell may lead to formation of local turbulence and should be avoided. Further, laminar flow within the flow cell is best achieved at some distance from entrance of the fluid into the flow cell. To this end, Weber and Prudy (*Anal. Chim. Acta* 100:531, 1978) have proposed the following Equation (3) for ensuring laminar flow at a distance from a flow cell entrance ($L_e$):

$$L_e \approx 0.05 \cdot R_e \cdot D_h \quad (3)$$

As mentioned in the background section above, the rise and fall times of a flow cell-based measurement (i.e., the time it takes for the sample concentration to rise from 0% to 100% over the sensing surface, and then fall back to 0%) limits the ability to resolve fast reaction kinetics. At the beginning and end of sample introduction, the sample is diluted by dispersion with the carrier solution (e.g., buffer). Thus, rather than instantaneous rise and fall times, there is some time lag due to dispersion of the sample. Such dispersion can, as a first approximation, be described by a first order kinetic process according to Equation (4):

$$\frac{dC}{dt} = k_{Lqx}(C_0 - C) \text{ or } \frac{dC}{dt} + k_{Lqx}C = k_{Lqx}C_0 \quad (4)$$

where $k_{Lqx}$ is the liquid exchange rate constant, $C_0$ is the concentration of the sample and C is the concentration of the sample at the sensing surface.

In the BIAcore instrument, the concentration of the sample at the sensing surface, C, is dominated by the dispersion in the flow cell. Multiplying Equation (4) with the integration factor $e^{k_{Lqx}t}$ and integrating the same gives the following Equation (5):

$$C = C_0(1 - e^{-k_{Lqx}t}) \quad (5)$$

This equation approximately describes the rise of the sample concentration at the sensing surface during a liquid exchange. The time required by the liquid exchange may, for example, be defined as the time to reach 99% of the final value. Using Equation (5), rise time may thus be expressed by Equation (6):

$$0.99 = \frac{C}{C_0} = \left(1 - e^{-k_{Lqx}t}\right) \Rightarrow \text{rise time} = t_{0.99} = \frac{4.6}{k_{Lqx}0.99} \quad (6)$$

Thus, if the rise time to 99% is known, the liquid exchange rate constant, $k_{Lqx}$, can be calculated from Equation (6). Similarly, the first order equation for the liquid exchange during the fall is described by Equation (7):

$$C = C_0 \cdot e^{k_{Lqx}t} \quad (7)$$

which gives the following Equation (8) for the time it takes to fall to 1% of the plateau value:

$$0.01 = \left(e^{k_{Lqx}t}\right) \Rightarrow \text{fall time} = t_{0.01} = \frac{4.6}{k_{Lqx}0.01} \quad (8)$$

To obtain an experimental relationship between rise time (or fall time) and flow rate, the rise time to 99% of the steady state concentration (or fall time to 0.01%) can be measured and plotted against sample flow according to Equation (9):

$$\text{Rise time} = \frac{V_a \cdot 60}{\text{Sample flow}} \quad (9)$$

where $V_a$ corresponds to the volume of sample (µl) that must be displaced during an exchange of fluid. In Equation (9), sample flow is expressed as a sample volume per unit time (µl/min), and the rise time is measured in seconds (hence the presence of the 60 sec/min conversion). Experimental results for representative flow cells of this invention are presented in Example 4. By determining $V_a$ from experimental data, Equation (9) may be used to calculate rise times for different sample flows.

Further, Equation (9) may also be used to obtain an expression for the time to rise to 99% of the original concentration. Combining Equations (6) and (9), the liquid exchange rate constant may be expressed as Equation (10):

$$K_{Lqx} = \frac{4.6}{\left(\frac{V_a \cdot 60}{\text{Sample flow}}\right)} \quad (10)$$

Under appropriate conditions, this equation may be used to calculate the liquid exchange rate constant for different flow cells. The larger $K_{Lqx}$, the faster the reaction kinetics that can be measured. A comparison of liquid exchange rates is presented in Example 4 for different flow rates through representative flow cells of this invention.

With regard to suitable flow cells for use in the practice of this invention, such flow cells may assume a number of forms, the design of which may vary widely depending upon the intended application and/or use. While several representative flow cells are disclosed herein for purpose of illustration, it should be recognized that any type of flow cell which is capable of contacting a liquid sample to a sensing surface under laminar flow conditions may be employed in the practice of this invention.

In one embodiment, a flow cell of this invention has two inlets and one outlet, such that two liquid streams enter the flow cell via their respective inlets and travel through the flow cell side-by-side and under laminar flow conditions, exiting the outlet. A sensing surface is located along a wall portion of the interior volume of the flow cell such that at least one of the liquid streams contacts the sensing surface. A representative flow cell of this embodiment is depicted in FIGS. 2A and 2B, and is referred to herein as a "Y flow cell."

Figure 2A:
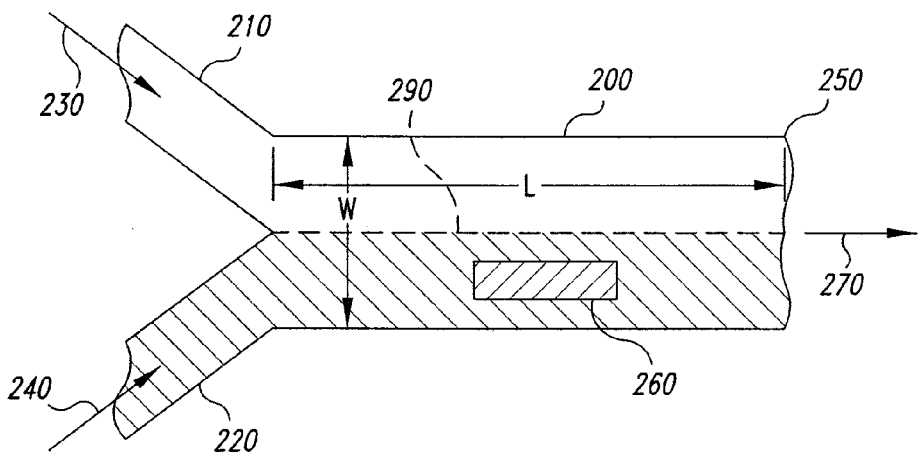
FIGS. 2A and 2B illustrate a Y flow cell with two laminar flows (one buffer flow and one sample flow).

Referring to FIG. 2A, a cross-sectional view of Y flow cell 200 is illustrated, having inlet arms 210 and 220 and outlet end 250. The flow cell has interior length l, width w and height h (not shown). A first fluid (such as a buffer), depicted by arrow 230, enters flow cell 200 via inlet 210, and a second fluid (such as a sample), depicted by arrow 240, enters via inlet 220 (in FIG. 2A, second fluid 240 is shaded for purpose of illustration). The first and second fluids travel length l of the flow cell under laminar flow conditions such that interface 290 separates first fluid 230 from second fluid 240, with both fluids exiting outlet end 250 of the flow cell as depicted by arrow 270.

Figure 2B:
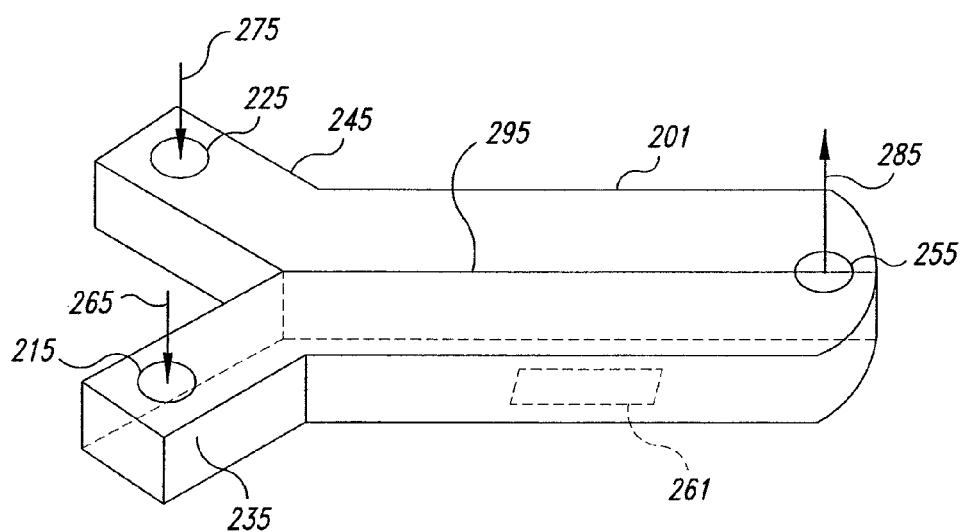

An isometric view of a representative Y flow cell is illustrated in FIG. 2B. In this figure, Y flow cell 201 has inlet arms 235 and 245, each containing inlets 215 and 225, respectively, and having a common outlet 255. A first fluid, represented by arrow 265 enters the flow cell via inlet 215, while a second fluid, represented by arrow 275 enters the flow cell via inlet 225. The two fluids travel in the direction of outlet 255 under laminar flow conditions such that interface 295 separates first fluid 265 from second fluid 275, with both fluids exiting outlet 255 as depicted by arrow 285.

As the two fluids travel through the Y flow cell illustrated in FIGS. 2A and 2B, at least one of the fluids comes in contact with a discrete sensing area along a wall portion within the interior volume of the flow cell, as depicted by sensing areas 260 and 261 in FIGS. 2A and 2B, respectively. The interaction between the fluid and the sensing area may involve a variety of interactions, as discussed in greater detail below. Such interactions may be detected by sensing techniques known to those skilled in the art which probe the sensing area from the "back side"—that is, from the opposite side of the sensing area in contact with the fluid. Alternatively, such interactions my be detected by sensing techniques which probe the sensing area from the "front side"—that is, from the side of the sensing area in contact with the fluid. Such detecting may be done at the same time that the fluid is in contact with the sensing area or at some subsequent time, and may be done while the sensing area is associated with the flow cell or separate therefrom.

Figure 3A:
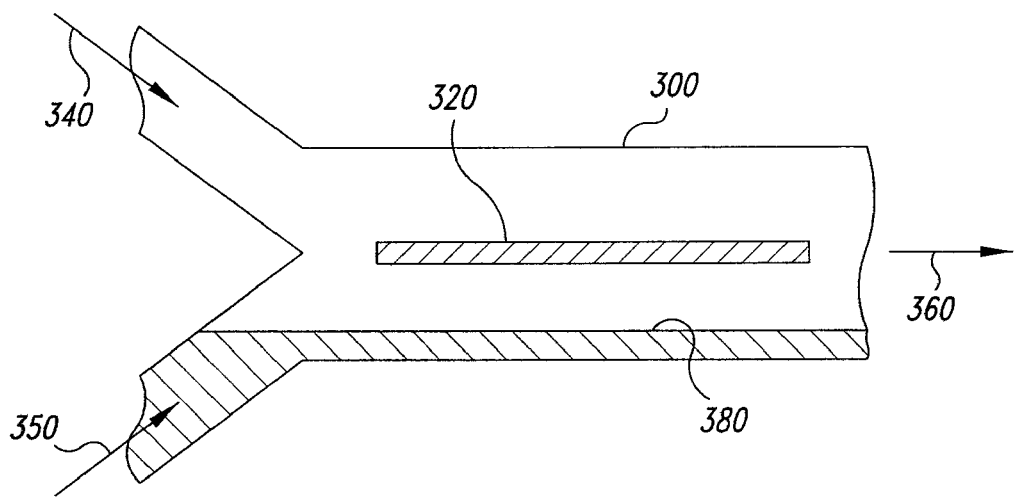
Figure 3B:
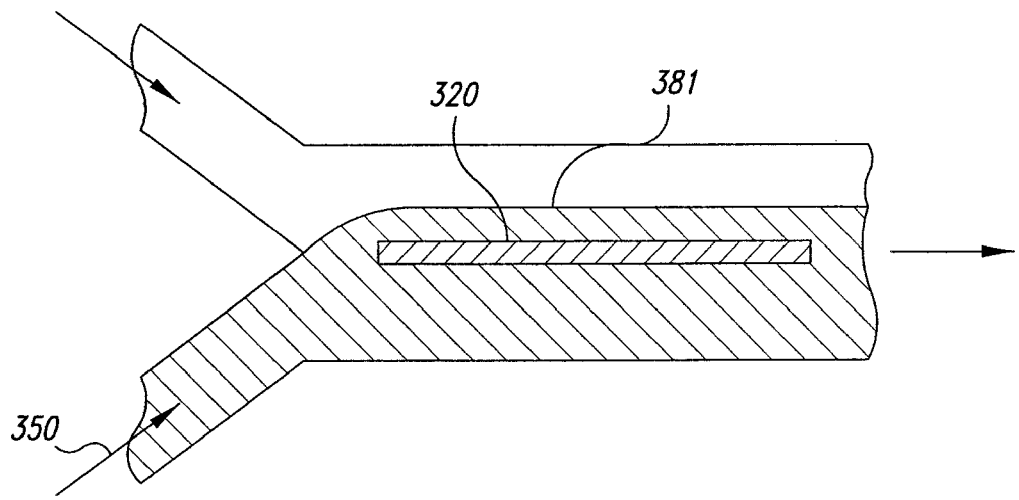
FIG. 3B shows the sample fluid covering the sensing area.

By employing at least two laminar flows, it is possible to guide the fluids within the flow cell in a controlled manner, thus bringing the first fluid (such as a sample) in selective contact with a sensing area within the flow cell. For example, FIG. 3A depicts flow cell 300 which is similar to the flow cell 200 of FIG. 2A, but having sensing area 320 located approximately along the center-line of the flow cell. In this embodiment, movement or displacement of the interface may be used to bring the sample flow into contact with the sensing area. More specifically, a sample flow (represented by arrow 350) and buffer flow (represented by arrow 340) enter the flow cell, travel the length of the flow cell under laminar flow conditions, and exit the flow cell as represented by arrow 360. For purpose of illustration, sample flow 350 is shaded. The flow rates of the sample and buffer flows are selected such that interface 380 is at a position within the flow cell such that the sample flow is not in contact with sensing area 320. The sample and/or buffer flow rates are then adjusted to displace interface 380 to position interface 381 as shown in FIG. 3B, thus bringing sample flow 350 into contact with sensing area 320. In this embodiment, the rise and fall times, as discussed above, are limited only by the movement of the interface from a first position not in contact with the sensing area (see interface 380 of FIG. 3A), to a second position such that the sample flow is in contact with the sensing area (see interface 381 of FIG. 3B). The volume of sample required to move the interface from the first to second positions is a fraction of the volume of the flow cell itself.

Figure 4A:
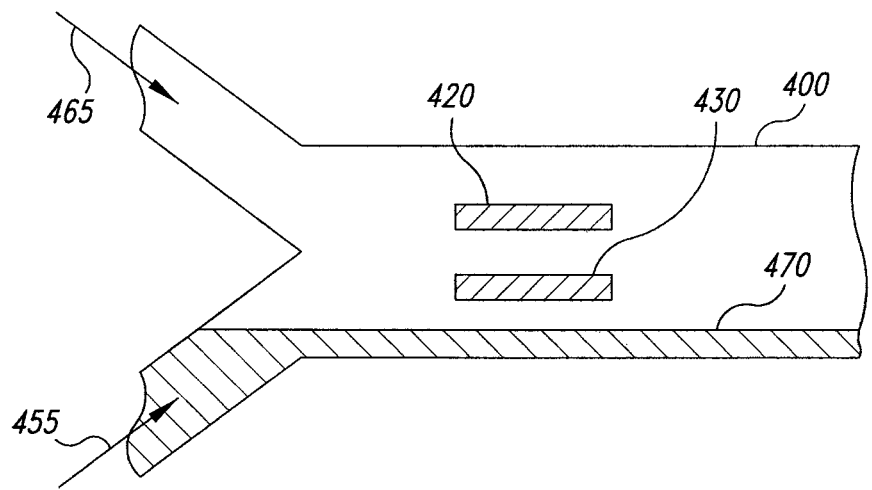
Figure 4B:
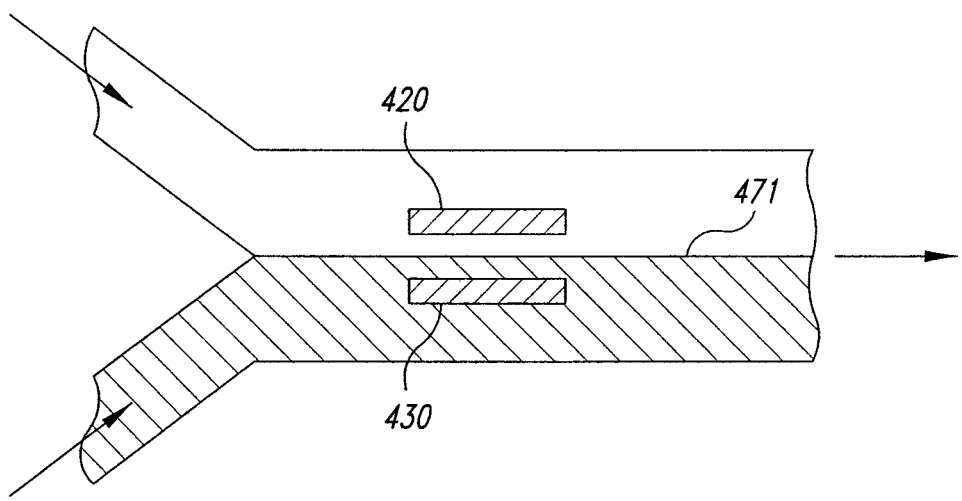
FIG. 4B shows the interface displaced such that the sample flow contacts one of the sensing areas.

In another aspect of this embodiment, multiple sensing areas may be employed within the flow cell. As illustrated in FIG. 4A, flow cell 400 has sensing areas 420 and 430, with sample flow (the shaded fluid depicted by arrow 455), buffer flow (depicted by arrow 465), and interface 470 such that the sample flow is not in contact with either of sensing areas 420 or 430. The flow rates of sample and buffer are then adjusted to bring sample flow 455 into contact with sensing area 430 by movement of interface 470 in FIG. 4A to a location between sensing areas 420 and 430, as represented in FIG. 4B as interface 471. The advantages of moving the interface in this manner are as discussed above in reference to FIGS. 3A and 3B. In addition, sensing area 420 in contact with the buffer flow can be used for a variety of purposes as discussed below, including use as an internal reference.

Figure 5A:
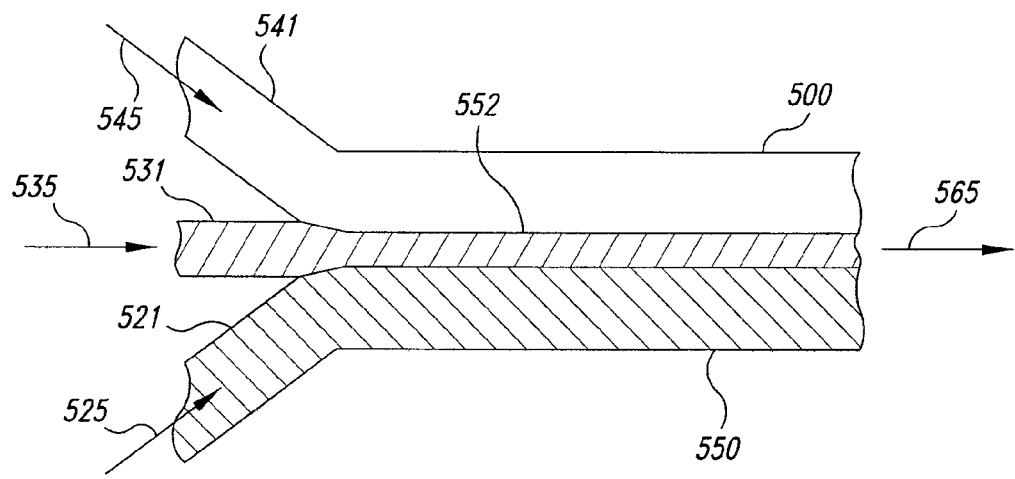
FIGS. 5A and 5B illustrate a representative Ψ flow cell having two buffer flow inlets and one sample flow inlet.
Figure 5B:
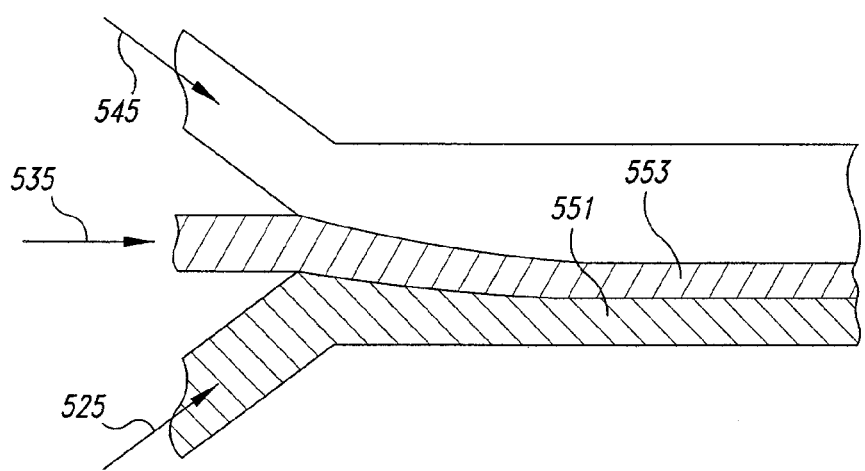

In another embodiment of this invention, a flow cell is disclosed having more than two inlets. Representative of this embodiment is a flow cell having three inlets as shown in FIG. 5A, also referred to herein as a "Ψ flow cell". Referring to FIG. 5A, sample flow (depicted by arrow 535) enters Ψ flow cell 500 by middle inlet 531. A first flow (as depicted by arrow 525) enters Ψ flow cell 500 via inlet 521, and a second flow (depicted by arrow 545) enters via inlet 541. All three flows travel through the flow cell, side-by-side and under laminar flow, and exit the flow cell as represented by arrow 565. Again for purpose of illustration, middle flow 535 and first flow 525 have been shaded. Thus, two interfaces 550 and 552 are present between the middle flow (e.g., sample flow) and the first and second flows (e.g., buffer flows). By adjusting the relative flow rates of the three flows, both the position and width of the middle flow may be selectively controlled. For example, as illustrated in FIG. 5B, middle flow 535 may be displaced toward the lower side wall of the flow cell by appropriate control of the flow rates of first flow 525 and second flow 545. Thus, interfaces 550 and 552 of FIG. 5A are shifted to locations 551 and 553, respectively, as shown in FIG. 5B.

At low linear flow rates, the flow through both the Y and Ψ flow cells is laminar and there is no active mixing of the fluid streams. In the context of the Y flow cell, the two fluids pass through the flow cell at a common flow rate, and the position of the interface is determined by the incoming flow rates. The following Equation (11) describes the situation in a thin layer flow cell (i.e., a flow cell with a rectangular cross-section and with w>>h:

$$\text{Interface} = w \cdot \frac{\text{First Flow}}{\text{First Flow} + \text{Second Flow}} \quad (11)$$

where w is the width of the flow cell and h is the height of the flow cell. Thus, by varying the first and second flow rates, the interface may be moved across the width of the flow cell.

With respect to the Ψ flow cell, location of the two interfaces under laminar flow conditions (i.e., "Interface 1" and "Interface 2") may be controlled in the flow cell by varying the first and second flow rates ("First Buffer Flow" and "Second Buffer Flow") and sample flow rate ("Sample Flow") as approximated by Equations (12a) and (12b).

$$\text{Interface 1} = w \cdot \frac{\text{First Buffer Flow} + \text{Sample Flow}}{\text{First Buffer Flow} + \text{Second Buffer Flow} + \text{Sample Flow}} \quad (12a)$$

$$\text{Interface 2} = w \cdot \frac{\text{Second Buffer Flow}}{\text{First Buffer Flow} + \text{Second Buffer Flow} + \text{Sample Flow}} \quad (12b)$$

where w is the flow cell width (and provided w>>h).

A more precise calculation of the position of the interface(s) requires correction of the above equations with the expression for the velocity profile (Brody et al., *Biophysical Journal* 71:3430-3441, 1996). The velocity profile is a parable with a velocity of zero close to the flow cell walls and maximum velocity in the middle of the flow cell. Directing a middle flow with two adjacent flows with equal flow rates places the middle flow in the center of the flow cell (as illustrated in FIG. 5A). However, if one of the two adjacent flow has flow rate of, for example, 5% of the total flow rate, this flow will actually occupy more than 5% of the cross sectional area of the flow cell. This is because the linear flow rate close to the flow cell wall is slower than the linear flow rate in the middle. The same volume flow rate requires a broader part of the flow cell close to the wall than at the middle of the flow cell.

Figure 6:
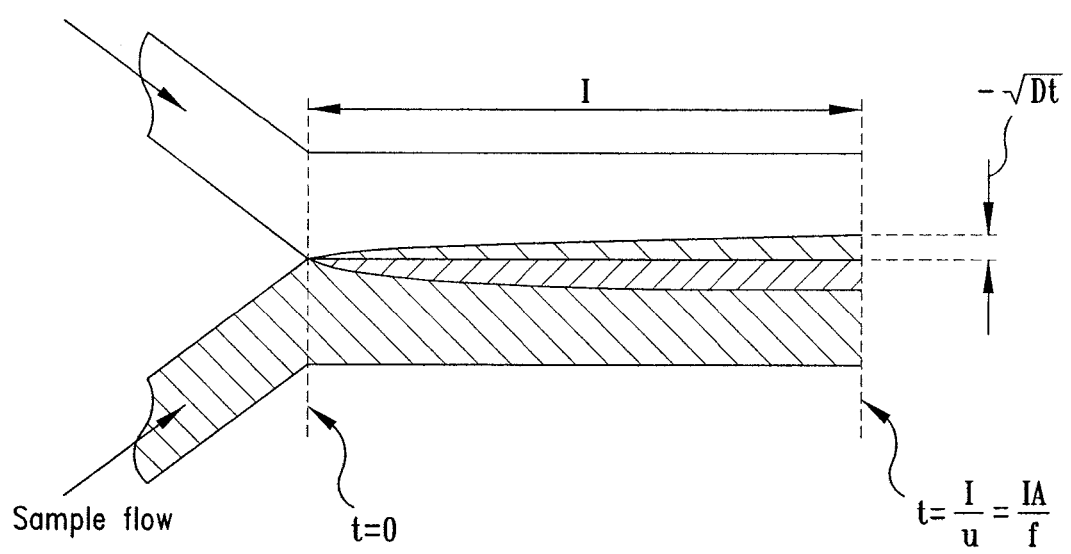
FIG. 6 represents diffusion in the Y flow cell over contact time, t, where f is the flow rate, L is the length of the flow cell, and A is the cross section area of the flow cell.

In addition, directing a sample flow within a flow cell using a separate flow (e.g., a buffer) requires that the diffusion of the sample be limited to the region close to the interface between the two flows. Otherwise, diffusion will interfere with the directionality of the sample flow and, rather than two (or more) distinct flows, a "smear" of sample and buffer will result. Since diffusion is a time-dependent process, the linear flow rates of the sample and buffer should be selected to limit diffusion in close proximity to the interface. Diffusion in a flow cell can be viewed as a one-dimensional phenomenon since the concentration gradient parallel to the interface is negligible. As long as the concentration at the side walls in the flow cell is constant, the width of the flow cell can be assumed to be infinite. The contact time at the interface is the same as the time it takes for the flow to transfer a molecule through the flow cell at a certain linear flow rate as illustrated in FIG. 6, where t is the contact time (sec.), f is the total volume flow rate ($m^3$/sec), A is the cross sectional area of the flow cell ($m^2$), u is the linear flow rate (m/sec) and D is the diffusion constant ($m^2$/sec). Thus, contact time can be expressed as the length of the flow cell divided by the linear flow rate, and the average diffusion width is approximately $\sqrt{Dt}$. The dark area of FIG. 6 corresponds to 100%, the gray area corresponds to 100-50%, and the light gray area corresponds to 50-0% of the original sample concentration.

The expression for concentration as a function of the distance and time is derived from Fick's second law, which has the solution of Equation (13) for the one-dimensional diffusion encountered with a Y flow cell:

$$c(x, t) = \frac{C_0}{2}\left(1 + \frac{2}{\sqrt{\pi}} \int_0^{\frac{x}{2\sqrt{Dt}}} e^{-\beta^2} d\beta\right) \quad (13)$$

In short, Equation (13) is the expression for concentration as a function of distance and time, where x (distance) is measured perpendicular from the interface (i.e., x is 0 at the interface). Similarly, in the context of the Ψ flow cell, the expression for the concentration as a function of distance and time is given by Equation (14):

$$c(x,t) = \frac{C_0}{2}\left(\frac{2}{\sqrt{\pi}}\int_0^{\frac{x-\text{Interface 1}}{2\sqrt{Dt}}} e^{-\beta^2}d\beta - \frac{2}{\sqrt{\pi}}\int_0^{\frac{x-\text{Interface 2}}{2\sqrt{Dt}}} e^{-\beta^2}d\beta\right) \quad (14)$$

Figure 7A:
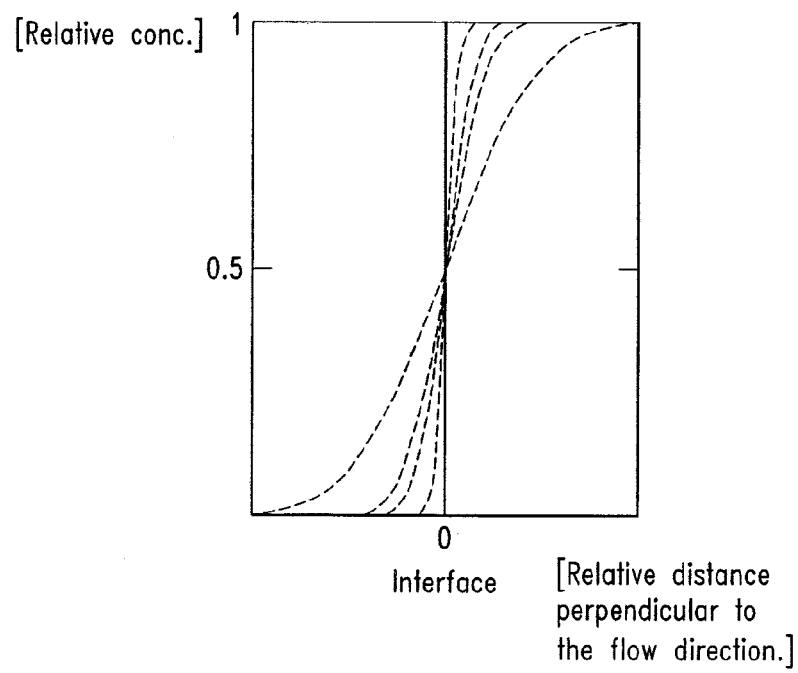
Figure 7B:
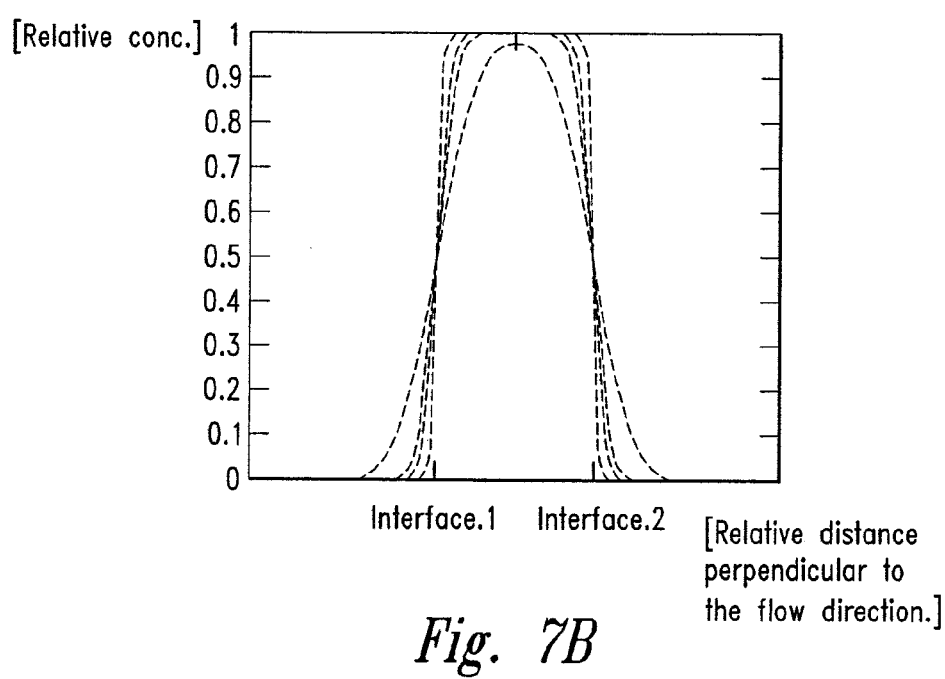
FIG. 7B shows the concentration of the sample at different contact times in a cross section of the Ψ flow cell.

FIGS. 7A and 7B are a graphical representations of Equations (13) and (14), respectively, for different contact times, where the x-axis is the distance x from the interface as discussed above, and the y-axis is the relative concentration (ranging from 0 to 100%).

In the preceding discussion, representative flow cells of this invention are disclosed which are capable of controlling laminar flow within the flow cell, particularly with respect to sample flow position and width. Such flow cells have a variety of uses. In one embodiment, the flow cell may be used to selectively contact a sample with a sensing area within the flow cell. In this manner, a flow cell having multiple sensing areas may be utilized, with the sample flow being selectively contacted with one or more of the sensing areas by the techniques discussed above. For example, FIGS. 4A and 4B discussed above illustrate a flow cell having two sensing areas, with sample flow being selectively contacted with one of the sensing areas. However, it should be recognized that multiple sensing areas may be employed, and that the sample flow may be selectively contacted with any of the sensing areas under conditions of laminar flow.

In another aspect, the sample flow contains a ligand which is used to sensitize a discrete sensing area within a flow cell. As used herein, "sensitize" or ("sensitization") means any process or activation of the sensing area that results in the sensing area being capable of specifically interacting with a desired analyte. The resulting surface is referred to herein as a "sensitized sensing area" or a "sensitized area."

As used herein, the terms "ligand" and "analyte" are to be construed broadly, and encompass a wide variety of interactions. For example, the sensing area of the flow cell may be sensitized by immobilization of an analyte-specific ligand thereto. Representative ligands in this context include, but are not limited to, the following (in the following list, a representative binding partner is parenthetically identified): antigen (specific antibody), antibody (antigen), hormone (hormone receptor), hormone receptor (hormone), polynucleotide (complementary polynucleotide), avidin (biotin), biotin (avidin), enzyme (enzyme substrate or inhibitor), enzyme substrate or inhibitor (enzyme), lectins (specific carboxyhydrate), specific carboxyhydrate (lectins), lipid (lipid binding protein or membrane-associated protein), lipid binding protein or membrane-associated protein (lipid), polynucleotide (polynucleotide binding protein), and polynucleotide binding protein (polynucleotide), as well as more general types of interactions such as protein (protein), protein (polynucleotide), polynucleotide (protein), DNA (DNA), DNA (RNA) and RNA (DNA) interactions, and interactions between small organic synthetic compounds and proteins or nucleic acids.

Suitable ligands also include various chemical compounds that may be used, for example, to build a chemical library, including bifunctional compounds. One skilled in the art will recognize that ligands of this invention, and the corresponding analyte present in the sample flow, include a wide range of molecules that may be used to generate a sensitized surface area to perform a variety of tasks including, but not limited to, binding, hybridization, combinational chemistry, and other complex formations on the sensing surface. All such interactions are included within the scope of analyte-ligand interactions as this term is used in the context of this invention. Further, such interactions include, but are not limited to, covalent as well as non-covalent forces, such as electrostatic, hydrophobicity, dispersion, van der Waals or hydrogen binding forces, or any combination of the same.

Figure 8:
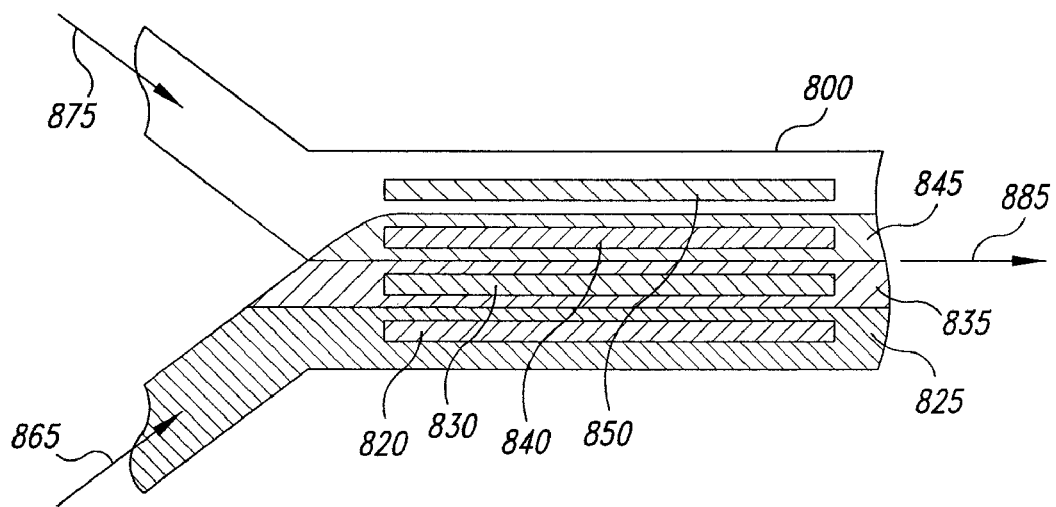
FIG. 8 illustrates formation of a gradient in the Y flow cell by changing the sample and buffer flow rate during sensitization of the sensing surface.
Figure 9:
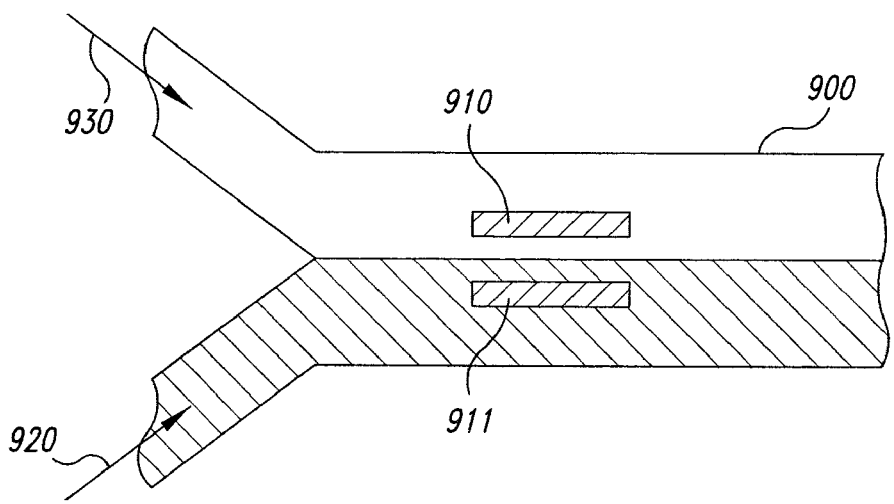
FIG. 9 illustrates a Y flow cell having two discrete sensing areas.

As noted above, the location of the sample flow within the flow cell, as well as the width of the sample flow, may be controlled in the practice of the invention. This permits immobilization of a ligand in a narrow row within the flow cell. For example, a gradient can be created within the flow cell by selectively directing sample flow over the sensing surface during immobilization of the ligand thereon. This aspect of the invention is illustrated in FIG. 8 wherein Y flow cell 800 contains sensing areas 820, 830, 840 and 850. Sample flow (depicted by arrow 865) and buffer flow (depicted by arrow 875) are introduced into the flow cell, and flow therein under laminar flow conditions, exiting the flow cell as represented by arrow 885. Initially, sample flow is only in contact with sensing area 820, with interface 825 between sample flow 865 and buffer flow 875 located between sensing areas 820 and 830. The sample and buffer flows are then adjusted to bring the sample flow into contact with sensing area 830, with interface 835 now located between sensing areas 830 and 840. This is then repeated to bring interface 845 between sensing areas 840 and 850, with sensing area 850 serving as a control. The length of time that the sample flows over sensing areas 820, 830 and 840 yields a gradient with regard to the amount of immobilized ligand bound to the surface of each sensing area. It should be noted that the various shades of gray of FIG. 8 are intended to illustrate the amount of bound ligand on each sensing area—that is, dark to light represents a higher amount of bound ligand to a lower amount of bound ligand. While this aspect of the invention is illustrated in FIG. 8 as a step gradient, a continuous gradient may similarly be generated In an alternative embodiment, a Y flow cell may be employed to sensitize discrete sensing areas with different ligands. As illustrated in FIG. 9, sensing areas 910 and 911 may be sensitized with different ligands by introducing a first sample flow containing a first ligand (depicted by arrow 920) into flow cell 900 under laminar flow conditions with a second flow (depicted by arrow 930). In this manner, sensing area 911 is sensitized with the first ligand. Second flow 930 may, in one embodiment, be a buffer flow or, in another embodiment, be a second sample flow containing a second ligand, in which case sensing area 910 is sensitized with the second ligand simultaneously with sensitization of sensing area 911 with the first ligand. When the second flow is a buffer flow, the buffer flow may be subsequently replaced with the second sample flow, in which case sensing area 910 is sensitized with the second ligand subsequent in time to sensing area 911 being sensitized with the first ligand. In this embodiment, the first sample flow may remain, or be substituted with a first buffer flow.

Figure 10:
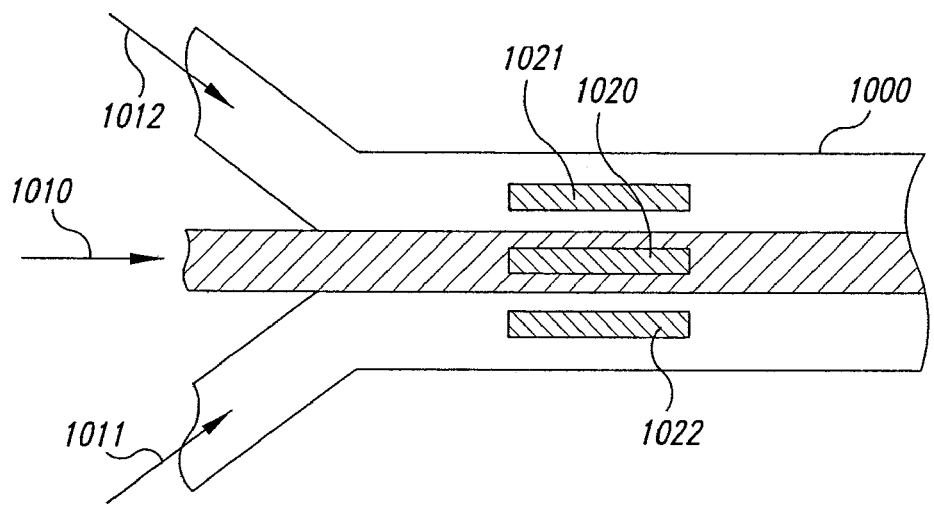
FIG. 10 illustrates a Ψ flow cell having three discrete sensing areas.

In the context of a Ψ flow cell, further sensitization permeations are possible. For example, two or more sensing areas may be sensitized with the same or different ligands by selectively positioning the sample flow containing the ligand within the flow cell. Thus, in one embodiment, three sensing areas may be sensitized with the same or different ligand as illustrated in FIG. 10. Referring to FIG. 10, a sample flow (depicted by arrow 1010 and shaded for purpose of illustration) containing a first ligand is directed within flow cell 1000 between a first and a second flow (depicted by arrows 1011 and 1012, respectively) such that sensing area 1820 is sensitized with the first ligand. Sensing areas 1021 and 1022 may then be sensitized by directing sample flow 1010 within the flow cell such that it contacts the desired sensing area, thereby sensitizing the same with the ligand contained within the sample flow. In this manner, a number of sensing areas may be sensitized within the flow cell by any number of desired ligands.

Figure 11A:
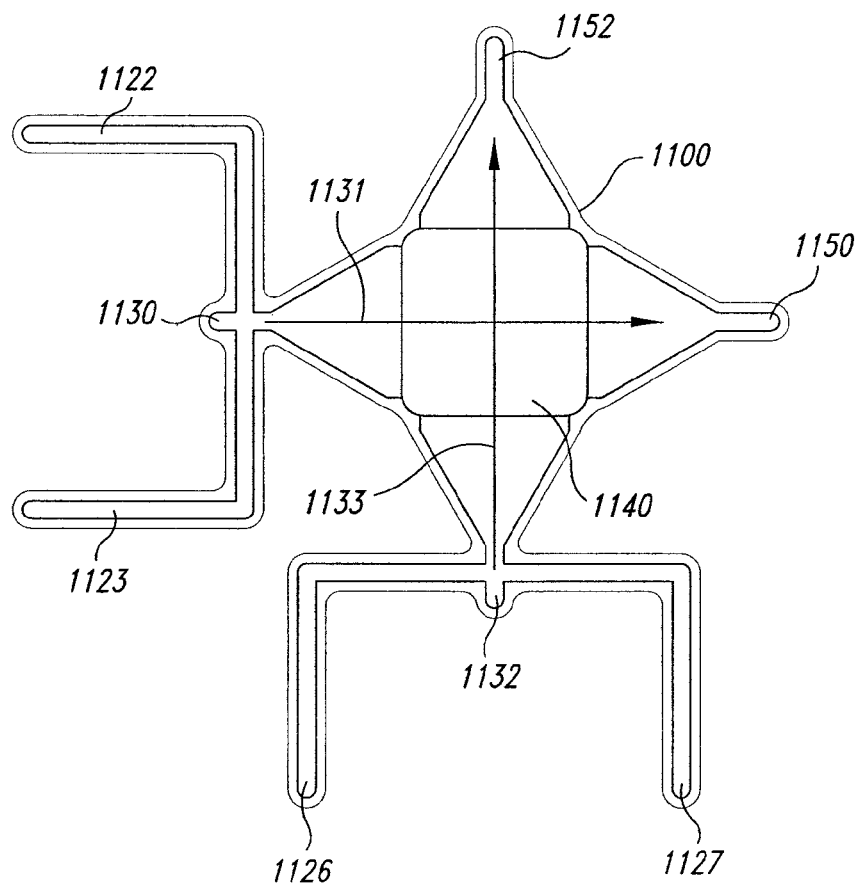
FIG. 11A illustrates a representative two-dimensional (2D) Ψ flow cell, with FIG. 11B depicting a cross-section thereof.

In a further embodiment, a second sample flow may be passed over the sensing surface within the flow cell at some angle, typically perpendicularly to a first sample flow, thereby generating overlapping sensing areas. This embodiment is generally referred to herein as a two-dimensional or "2D" flow cell. Use of such 2D flow cells in the practice of this invention permits sensitization of overlapping sensing areas within a flow cell. A representative 2D flow cell of this invention is illustrated in FIG. 11A. This figure represents the combination of two Ψ flow cells (a "2D Ψ flow cell"), such that the sample flows are at right angles to each other. While FIG. 11A depicts a 2D Ψ flow cell, it should be understood that a 2D Ψ flow cell may similarly be employed, or a 2D Ψ flow cell having more inlets than the six depicted in FIG. 11A (i.e., 3 inlets times 2 Ψ flow cells), or any combination of Y and Ψ flow cells having any number of inlets.

Figure 11B:
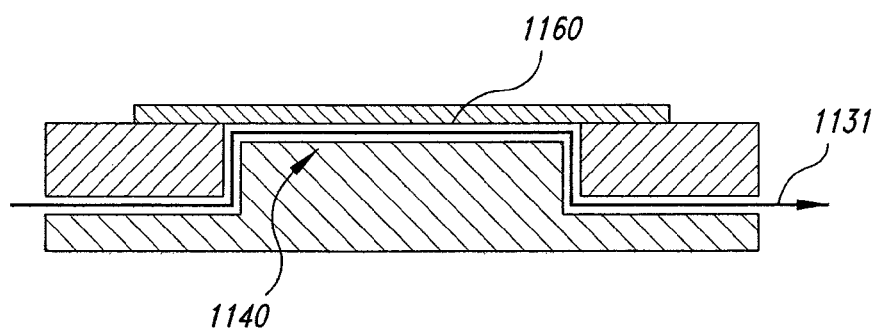

Referring to FIG. 11A, flow cell 1100 has buffer inlets 1122, 1123, 1126 and 1127, and sample inlets 1130 and 1132. A first sample flow (depicted by arrow 1131) passes through the flow cell and exists via outlet 1150. Similarly, a second sample flow (depicted by arrow 1133) can be applied sequentially by passing through the flow cell at an angle relative to the first sample flow, in this case perpendicularly, and exits via outlet 1152. Location and width of the first and second sample flows are controlled in the manner disclosed above with regard to the Ψ-flow cell. Referring to FIG. 11B, a side view of FIG. 11A is presented. The flow cell has a central plateau 1140 which directs the first and second sample flows to contact sensing surface 1160. In the case of FIG. 11B, first sample flow 1131 is depicted.

Figure 12A:
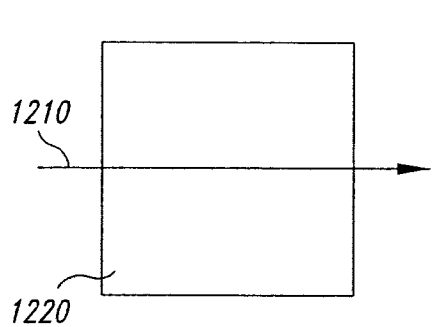
FIGS. 12A through 12E illustrate generation of sensitized rows on the sensing surface, and an overlapping sensing area.
Figure 12B:
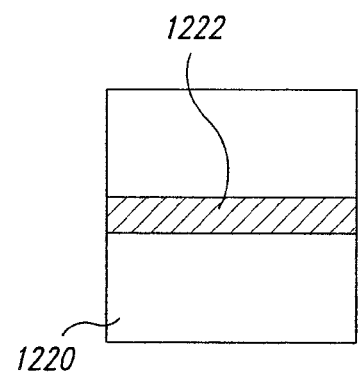
Figure 12D:
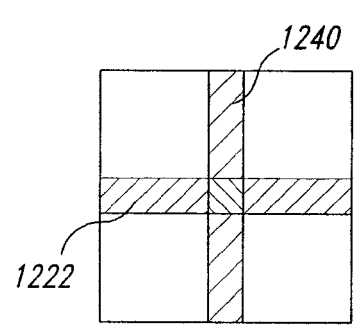
Figure 12C:
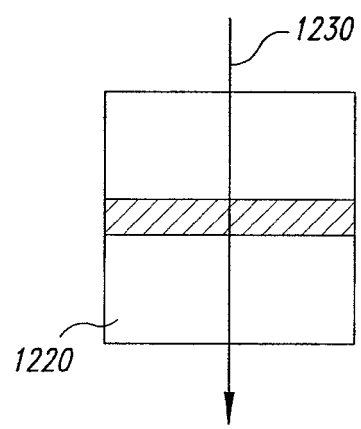
Figure 12E:
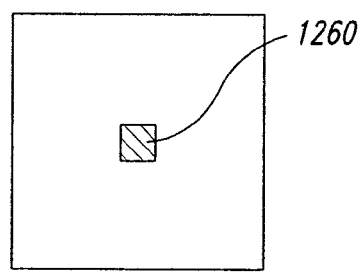

By employing a flow cell of this invention, a wide variety of sensitized sensing areas may be generated. For example, the 2D Ψ flow cell of FIG. 11A may be used to make sensitized matrices as illustrated in FIG. 12. FIG. 12A shows a sample flow (depicted by arrow 1210) containing a first ligand being directed across sensing surface 1220 to yield sensitized area 1222, as shown in FIG. 12B. A second sample flow containing a second ligand is directed across sensing surface 1220 as depicted by arrow 1230 of FIG. 12C, to yield sensitized area 1240, as represented in FIG. 12D, which overlaps with sensitized area 1222. This overlapping area is thus sensitized with two different ligands applied sequentially.

It will be recognized that such selective sensitization of a sensing surface permits a multitude of sensitization options. For example, to the extent that the second ligand contained within second sample flow 1230 of FIG. 12C interacts with the first ligand of sensitized area 1222, the resulting overlapping area 1260 may be depicted as in FIG. 12E. In short, a discrete area upon the sensing surface has been sensitized with a first ligand, followed by a second ligand. If the first ligand is, for example, a bifunctional reagent immobilized on the sensing surface, the second ligand may react with the immobilized reagent to yield an area or "spot" on the sensing surface that has been selectively modified with an immobilized bifunctional reagent (i.e., the first ligand), with a second ligand bond thereto.

Figure 13A:
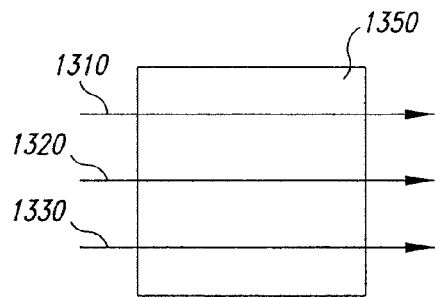
FIGS. 13A through 13E illustrate generation of a sensitized matrix of the present invention.
Figure 13B:
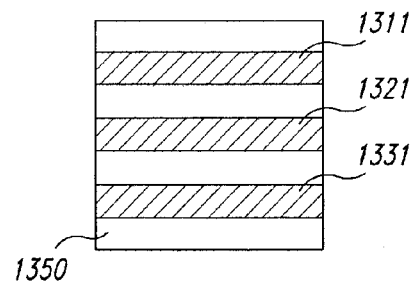
Figure 13D:
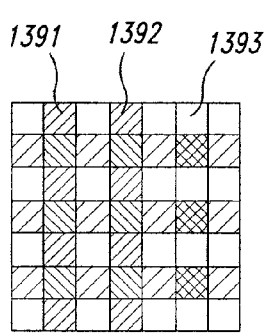
Figure 13C:
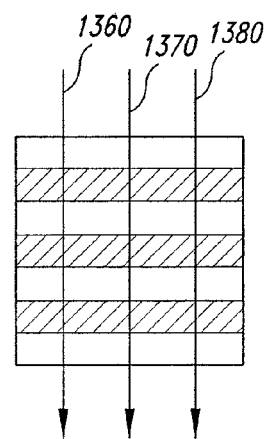
Figure 13E:
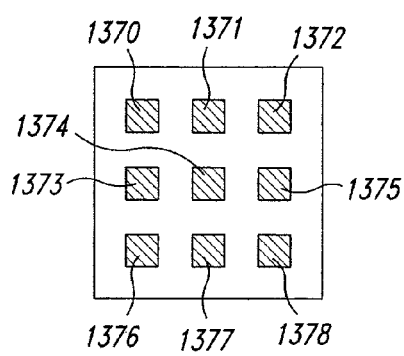

Similarly, as illustrated in FIG. 13A, by directing different flows (depicted by arrows 1310, 1320 and 1330), each containing a different ligand, sensitized areas 1311, 1321 and 1331 of three different immobilized ligands are generated on sensing surface 1350 as shown in FIG. 13B. Referring to FIG. 13C, three sample flows depicted by arrows 1360, 1370, and 1380, each contain the same or different ligands, are directed across sensing surface 1350, yielding sensitized areas 1391, 1392 and 1393. In this manner, each overlapping sensitized area of FIG. 13D is analogous to the sensitized surface depicted in FIG. 12D, and may further be represented as sensitized areas 1370 through 1378 as shown in FIG. 13E.

Figure 24A:
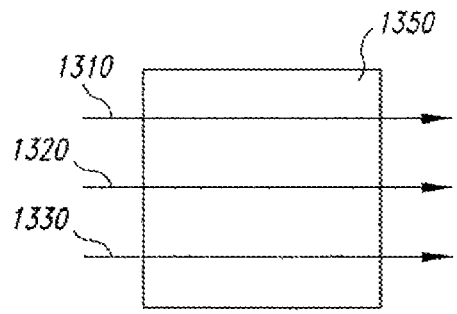
FIGS. 24A through 24F illustrate generation of a sensitized matrix according to one embodiment of the invention.
Figure 24B:
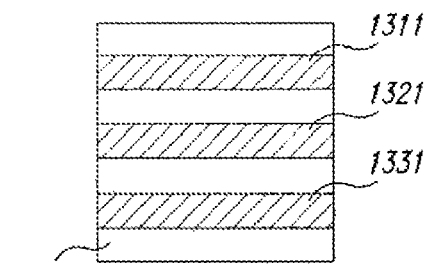
Figure 24C:
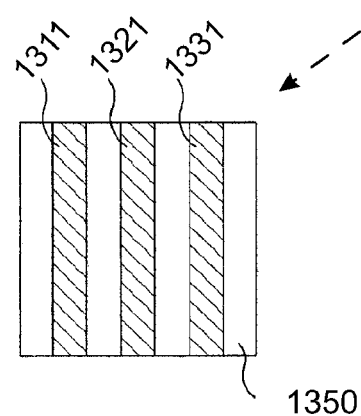
Figure 24D:
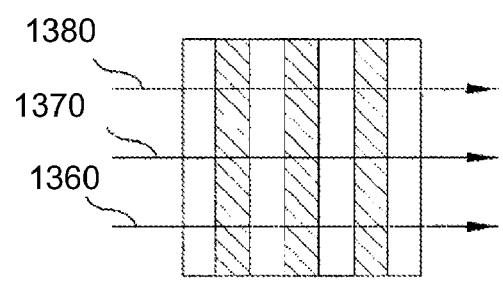
Figure 24E:
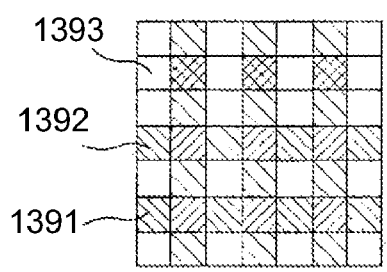
Figure 24F:
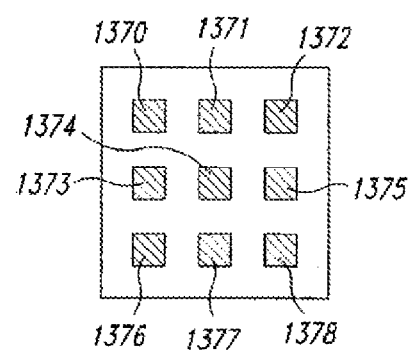

Further, as is schematically disclosed in FIGS. 24A-24F, a two-dimensional flow pattern over the sensor surface may be achieved using an one-dimensional flow cell wherein the sensing surface and the flow cell are turnably arranged with respect to each other to permit fluid flow over the sensing surface in a first direction and in a second direction in an angular relationship to the first direction. In this embodiment, the provision of a flow in the first direction is shown in FIG. 24a and the provision of a flow in the second direction is provided by a rotation of the sensing surface with respect to the flow cell indicated in the transfer from FIG. 24b to FIG. 24c by the turning arrow. According to one embodiment, there is provided a sensor device comprising a flow cell having an inlet end and an outlet end, at least one sensing surface on a wall surface within the flow cell located between the inlet and outlet ends, wherein the sensing surface is turnably mounted within the flow cell to permit it to be passed by fluid flow in a first direction and in a second direction in an angular relationship to the first direction.

One skilled in the art will readily appreciate the wide range of applications that such a two-dimensional matrix affords. Basically, any interaction that may be captured at discrete locations on the sensing surface of the flow cell may be measured. For example, a representative interaction is that of DNA sequencing by hybridization wherein the matrix may be prepared by the following coupling procedures using laminar fluid flows in two dimensions as disclosed above. First, the sensor surface (such as a dextran-coated surface having streptavidin bound thereto) has a ligand immobilized thereon (such as biotinylated DNA oligonucleotides) in defined bands 1311, 1321 and 1331 as illustrated in FIG. 13B. Such bands are generated by passing sample flows 1310, 1320 and 1330 over sensing surface 1350 as illustrated in FIG. 13A, with each sample flow containing a different biotinylated oligonucleotide. Complementary DNA oligonucleotides are then directed across the sensor surface as illustrated by arrows 1360, 1370 and 1380 in FIG. 13C, yielding a pattern of immobilized complementary DNA oligonucleotide as shown in FIG. 13E, wherein each area (1370 through 1378) represents a different immobilized complementary DNA.

The liquid flow containing the active reagent can be positioned to any width, from the whole width of the sensor area to very narrow dimensions. Different liquids and reaction conditions can be applied in the liquid streams that position the reagents. Such situations can be used to protect active intermediates formed when neighboring lines are formed before the second dimension reagents are introduced. In fact, this invention may be used to perform any kind of chemical syntheses on defined areas on a sensor surface. Organic solvents may be used where reagents are difficult to dissolve in water. It is also possible to use the diffusion of substances from organic solvents into water phases in the flow system in order to protect, for example, proteins from denaturation in contact with organic liquids. Further, chemical libraries can be produced by stepwise reactions on sensor surfaces. Complex molecules may be built with relatively few molecular building blocks. This invention may also be used for building polymers in defined areas on a sensor surface, such as peptides or oligonucleotides, in defined sequences. By using protection or deprotection in the different dimensions, as well as larger or smaller areas for the activation, defined sequences can be built.

Another application of this invention is for studying how multiple biomolecular complexes are formed and how they function. One example is epitope mapping of an antigen to find the binding sites for a series of antibodies in relation to each other. By the procedure described for two-dimensional building of reaction areas, epitope mapping may thus be performed. This can, for example, be done by directly measuring the interactions for the formation of complexes by techniques such as SPR detection, or analysis of bound material after the last molecule has been introduced by fluorescence. An exemplary procedure is as follows: on a surface covered with RAMFc antibody, different lines are formed in one direction for all analyzed antibodies directly from culture fluid; the whole surface is covered by blocking antibody by one interaction by an irrelevant antibody; the whole surface is covered by antigen that absorbs to all lines with immobilized primary monoclonal antibody; in the second dimension, the same antibodies are introduced and the formed complex for the second interaction for each area is measured; and regeneration of the whole surface is performed. Another situation of a similar type is when a series of, for example, proteins form an active complex and the order of adsorbing substances is critical. Different combinations of substance introduction can be introduced and the resulting reaction pattern observed.

In a further aspect of this invention, sensing surfaces are disclosed having one or a multiple of sensitized sensing areas thereon. Such sensing surfaces may be used for a wide variety of applications. For example, such surfaces may be sensitized with a different ligand at each sensitized area. A sample may then be contacted with all the sensitized areas and, based on the position of the sensitized area on the sensing surface, interaction between the sample and any given ligand determined. Contacting the sensing surface with the sample in this embodiment need not occur within a flow cell since the entire surface may be contacted with the sample. Alternatively, if selective contacting of the sensing surface with the sample is desired, such contacting may occur within a flow cell of this invention.

In another aspect of this invention, a sample flow is directed by laminar flow techniques over a sensing surface having one or more discrete sensing areas. As discussed above with regard to sensitization with a sample flow containing a ligand, a sample flow containing an analyte (as opposed to a ligand) may be directed by the laminar flow techniques of this invention across a sensitized surface (which can be sensitized by the laminar flow technique of this invention or other techniques) thereby allowing interaction with ligands on the sensing area. The laminar flow techniques described herein achieve extremely fast rise and fall times which make it possible to measure fast reaction kinetics in addition to standard binding analysis.

In this regard, and in one embodiment of this invention, movement of the interface may be used to bring a sample flow containing an analyte into contact with a sensing area. This may be illustrated by reference to FIG. 3A. Referring to that figure, Y-flow cell 300 has sensitized sensing area 320, and sample flow (the shaded fluid depicted by arrow 350) and buffer flow (depicted by arrow 340) are adjusted such that interface 380 is at a position within the flow cell such that the sample flow is not in contact with the sensitized sensing area. The sample and buffer flow rates are then adjusted to move the interface to position 381 as shown in FIG. 3B, thus bringing sample flow 350 into contact with sensitized sensing area 320. In this embodiment, the rise and fall times, as discussed in greater detail above, are limited only by the movement of the interface from a first position not in contact with the sensing area (see FIG. 3A), to a second position such that the sample flow is in contact with the sensing area (see FIG. 3B). The volume of sample required to move the interface from the first to second positions is a fraction of the volume of the flow cell itself. Thus, instead of shifting from buffer flow to sample flow with valves at some distance from the sensing area (e.g., a volume of about 0.5 μl for the BIAcore instrument), the interface can be moved with only a fraction of the volume of the flow cell (e.g., 0.05 μl). Since the rise time is proportional to the volume that has to be displaced, a tenfold decrease in volume reduces the rise time by about 10 fold. Similar advantages are achieved with shorter fall times.

Such fast rise and fall times are of necessity when measuring fast reaction kinetics. For example, the techniques of this invention may used to study association and dissociation. In one embodiment, an analyte may be passed over a sensitized sensing area. The sample flow may then be displaced from contact with the sensitized sensing area, and the dissociation rate can be detected. Alternatively, a sample flow may be rapidly displaced onto a sensitized sensing area, thereby allowing for the detection and analysis of association kinetics.

In another embodiment of this invention, multiple sensing areas may be employed within a single flow cell for purposes of analysis. In one aspect, the flow cell may contain two sensing areas. As illustrated in FIG. 4A, flow cell 400 has sensing areas 420 and 430, with sample flow containing analyte (the shaded fluid depicted by arrow 455), buffer flow (depicted by arrow 465), and interface 470 such that the sample flow is not in contact with either of the sensing areas. The flow rates of buffer and sample are then adjusted to bring sample flow 455 into contact with sensing area 430 by movement of interface 470 to a location between sensing areas 420 and 430, as depicted in FIG. 4B as interface 471. The advantages of moving the interface in this manner are as discussed above. Further, because the multiple sensing areas are located in close proximity within the same flow cell, time lag and temperature variations between the two sensing areas are negligible, which increases the reliability and accuracy of sample analysis.

Moreover, the ability to control location of the sample flow within the flow cell, in combination with multiple sensing areas, permits a wide range of applications. For example, still referring to FIGS. 4A and 4B, sensing area 420 may be a non-sensitized or sensitized sensing area. Thus, sensing area 420 of FIGS. 4A and 4B may be used as a non-sensitized or blank control (i.e., with no surface immobilized ligand), or a sensitized control (i.e., with immobilized ligand bound thereto). A blank control can detect non-specific binding to the sensing area (e.g., to the dextran matrix), while a sensitized control will provide information about non-specific binding to both matrix and immobilized ligand. In this manner, bulk effects and non-specific binding can be "subtracted out". Such subtraction is best achieved when the immobilization levels of the ligand are the same for the sensitized sensing area and sensitized control. This is particularly important when high immobilization levels are used (e.g., when the analyte is a small molecule). This aspect of the invention is further illustrated in Example 5.

Figure 14A:
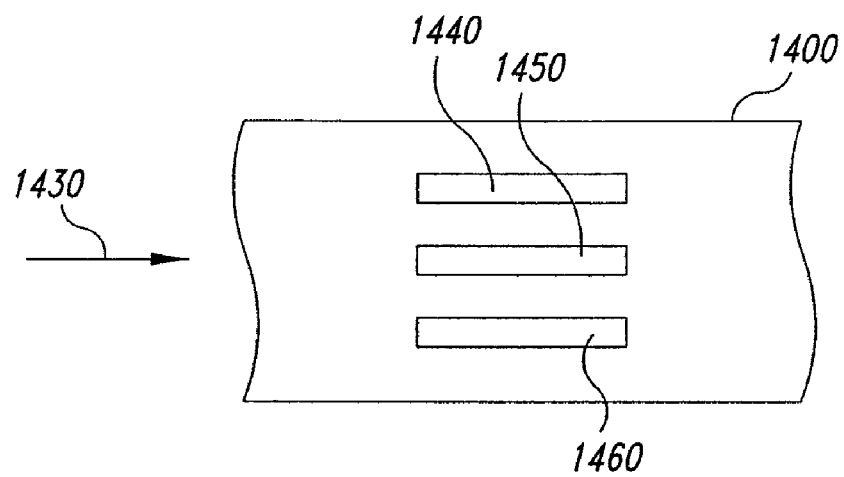
FIG. 14A illustrates a flow cell having two sensitized areas and one non-sensitized area, with sample flow contacting all three areas.
Figure 14B:
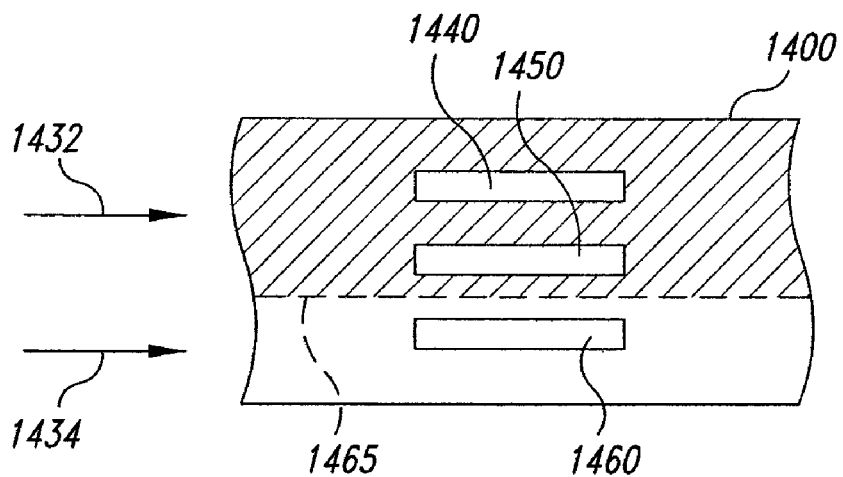
FIG. 14B illustrates an alternative embodiment having two sensitized areas and one non-sensitized area, with sample flow contacting one sensitized area and the non-sensitized area.

In another embodiment of this invention, multiple sensing areas may be employed in a variety of methods. For example, as illustrated by FIGS. 14A and 14B, flow cell 1400 may have ligand immobilized on sensitized sensing areas 1440 and 1460, and non-sensitized sensing area 1450. The ligand immobilization may be accomplished using techniques described above to direct the sample flow containing the ligand over the sensing surface. However, one skilled in the art will recognize that sensitization of the sensing areas, prior to probing with sample flow containing analyte, may be effectuated by methods other than the laminar flow techniques herein disclosed. For example, discrete sensitized sensing areas may be made by currently known techniques, such as surface modification techniques using masking (e.g., photolithography). A sample flow containing an analyte may then be directed into the flow cell as represented by arrow 1430, such that the sample flow contacts sensing areas 1440, 1450 and 1460. In this manner, non-sensitized sensing area 1450 may serve as a control, and sensitized sensing areas 1440 and 1460 may have the same or different ligands associated therewith. This technique has particular advantage in analysis of fluids containing multiple analytes, such as analysis of body fluids, which analytes could be analyzed simultaneously using this technique.

Alternatively, as illustrated in FIG. 14B, flow cell 1400 may have ligand immobilized on sensitized sensing areas 1450 and 1460, with sensing area 1440 serving as a non-sensitized control. Both a sample flow, containing analyte, (depicted by arrow 1432 and shaded for purposes of illustration) and a buffer flow (depicted by arrow 1434) may be directed into the flow cell such that the sample and buffer flow interface 1465 is between sensing areas 1460 and 1450. In this manner, sensitized sensing area 1450 serves as the principle analyses area, with sensing areas 1440 and 1460 both serving as controls (i.e., sensing area 1440—sample flow, no immobilized ligand; sensing area 1460—buffer flow, with immobilized ligand). In this embodiment displacement of the sample flow containing the analyte over multiple discrete sensing areas can be accomplished. Therefore, independent analysis of analytes contained within a sample flow may be done nearly simultaneously by merely displacing the sample flow over the sensing area of interest. This could also be accomplished using multiple buffer and sample flows.

The above techniques also allow for the detection of ion exchange in the flow cell (see Example 3). More specifically, diffusion over the interface can be used for membrane-free dialysis (e.g., small molecules will diffuse across the interface faster than large molecules). By employing a chromatography eluent (e.g., in-line or sample fractions) as the sample flow, the salt content (e.g., ionic exchange chromatography) or organic solvent content (e.g., reverse phase chromatography) will vary. This variation permits direct detection by injection and in-situ dialysis in the flow cell, thus avoiding dilution or pre-dialysis of the sample.

In a further embodiment, an analyte that is difficult to solve in a water phase may be passed through the flow cell in an organic sample flow, allowed to diffuse into an adjacent water flow, and then used in one or more of the techniques set forth above.

The following examples are offered by way of illustration, not limitation.

EXAMPLES

Example 1

Representative Flow Cells

This example discloses representative flow cells, as well as the use thereof in the context of this invention. In particular, different Y and Ψ flow cells are illustrated.

Figure 15:
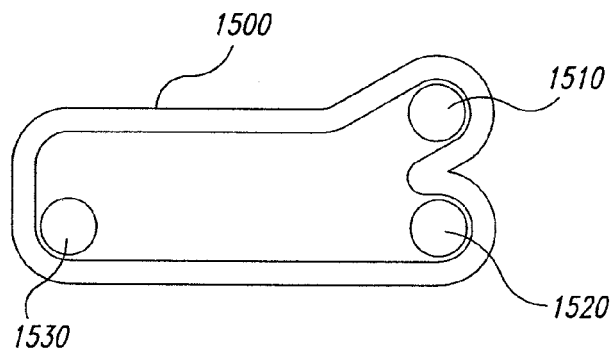
FIG. 15 depicts a representative Y flow cell.

A representative Y flow cell uses the inlets to flow channels 1 and 2, and the outlet to flow channel 2 of a commercially available IFC 4 for a BIAcore 1000 system (BIACORE AB, Uppsala, Sweden). Referring to FIG. 15, sample flow enters Y flow cell 1500 from inlet 1510, and the buffer enters the Y flow cell from inlet 1520. Both sample and buffer exit the Y flow cell via outlet 1530. Both sample and buffer flows are directed into the flow cell by cutting an additional channel in the IFC 4 to allow both sample and buffer to be run through the flow cell simultaneously. The volume of the Y flow cell is 180 nl (i.e., three times the volume of commercially available BIAcore flow cells).

Figure 16:
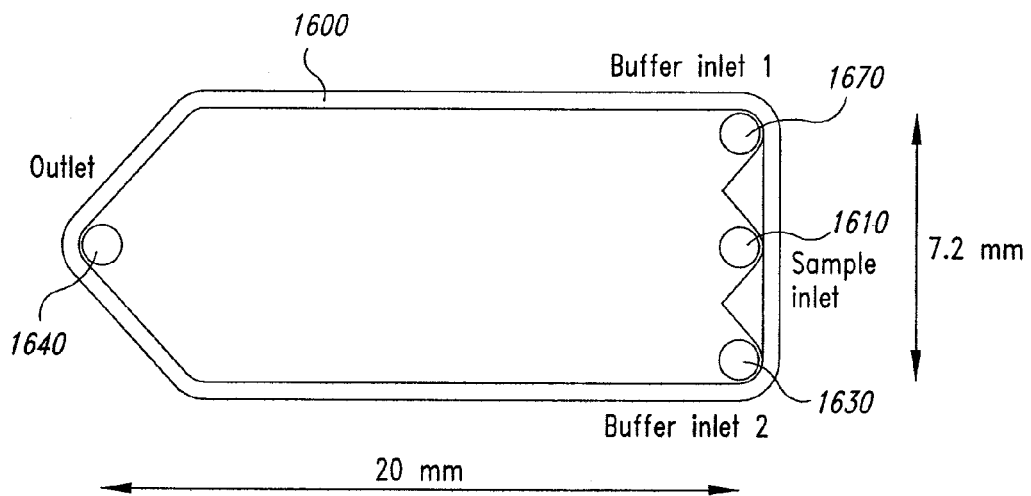
FIG. 16 illustrates a representative one-dimensional (1D) Ψ flow cell.

A representative one dimensional ("1D") Ψ flow cell is depicted in FIG. 16, where sample flow enters Ψ flow cell 1600 via inlet 1610, with buffer flows entering by inlets 1670 and 1630, and all flows exiting outlet 1640. The Ψ flow cell is made in PMMA, and employs Pharmacia 500 pumps with 500 μl Hamilton syringes for delivery of fluid flow to the flow cell.

Example 2

Diffusion of Fluid Flows

This example summarizes experiments directed to diffusion of fluid flows as they pass through the representative Ψ flow cell of Example 1. As mentioned above in the context of FIG. 6, directing fluid flows within a flow cell under laminar flow requires diffusion of the sample to be limited to a region close to the interfere between the flows. If this is not the case, diffusion will interface with the directionality of the sample flow and, rather than distinct flows, a "smear" of flows will result.

Figure 17A:
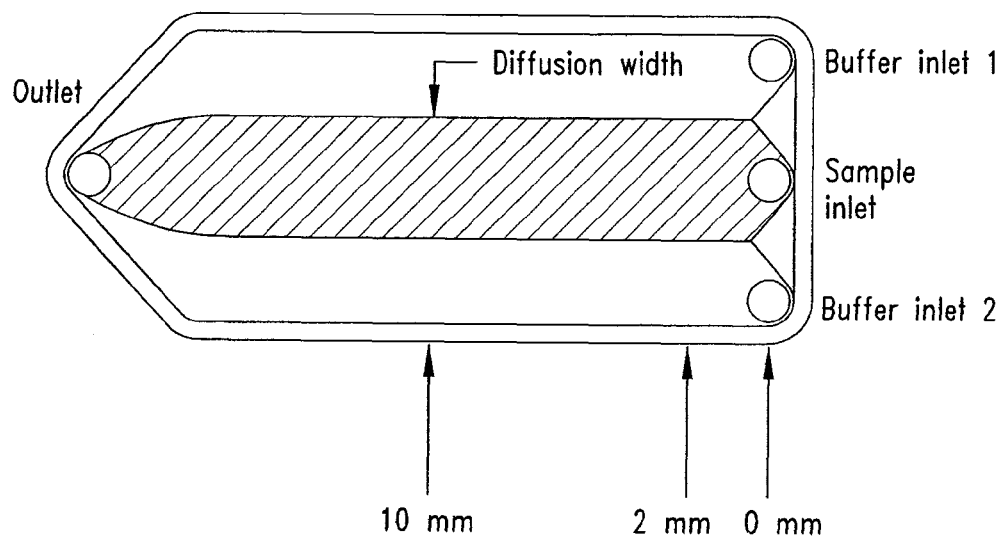
FIG. 17A illustrates the diffusion width of the 1D Ψ flow cell as measured at 2 mm and 10 mm from the inlet for different flow rates (i.e., different contact times), and FIG. 17B graphs the diffusion width versus the contact time.
Figure 17B:
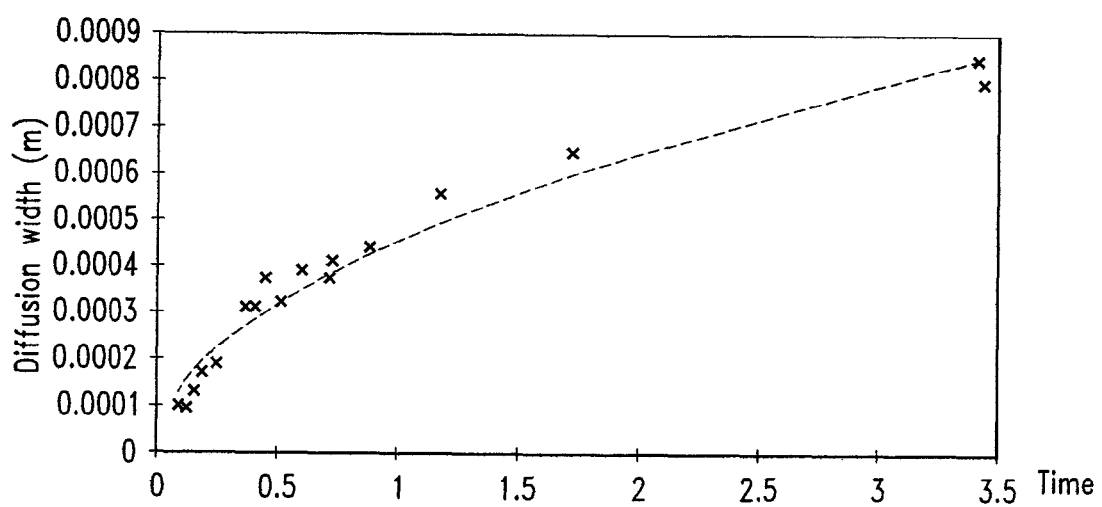

In this experiment, diffusion width is determined after about 0.3 seconds, which is the time it takes to transport a molecule through the flow cell of the BIAcore instrument at a flow rate of 10 μl/min. The diffusion width (see FIG. 17A) was measured as the width of a color change of an indicator as measured by ocular inspection with a Panasonic WV-Ks 152 video camera and a microscope mounted to the work processor. The diffusion width for different contact times at the interface was fitted with $\sqrt{Dt \cdot C}$, where C is a dimensionless constant fitted for each pH (see FIG. 17B). The experimental diffusion width was then estimated for different contact times from the fitted constant C.

Table 1 shows the experimental results and the theoretically calculated values for the diffusion of protons. The theoretical values are calculated with Equation (14). The pH change required to obtain a color shift was measured with a pH meter and ocular inspection. In these experiments, the required pH change was 0.4 pH units for phenol red (PR) and 0.6 pH units for bromophenol blue (BB). Since concentration change perceived as a color change in a 100 ml container may not be the same as for a thin layer flow cell, the theoretical diffusion width for BB is calculated for three different concentration changes (i.e., pH shifts). The column "diffusion of indicator" in Table 1 describes the broadening of the color change band due to the diffusion of indicator into the acid fluid. The errors in the PR and the BB part of Table 1 show an increasing tendency as the pH difference between the two fluids decreases. This behavior is believed to be due to a flattening of the concentration gradient as the concentration difference between the two fluids decreases. A steep concentration gradient makes a sharp color change, while a flat concentration gradient makes a diffuse color change. Consequently, an incorrect estimation of the required pH change for a color shift will give increasing errors as the concentration difference between the two fluids decreases.

TABLE 1

Diffusion of Protons into the Indicators Phenol Red and Bromophenol Red

Phenol Red 2.8 mM (pKa = 7.9, D = 3.4 * $10^{-10}$)

| | Experimental | | Theoretical | | | | Error | |
|---|---|---|---|---|---|---|---|---|
| HCL pH | C | Exp. width (µm)] | PH change | Conc. change (%) | Theo. width (µm)-] | Indicator diffusion (µm) | Absolute | Relative |
| 0.086 | 4.6 | 249 | 0.4 | 22.5 | 243 | 16 | −10 | −0.04 |
| 1.08 | 3.5 | 189 | 0.4 | 22.5 | 187 | 16 | −14 | −0.07 |
| 1.9 | 2.9 | 157 | 0.4 | 22.5 | 127 | 16 | 14 | 0.09 |
| 1.04 (20% Glycerol) | 2.8 | 157 | 0.4 | 22.5 | 144 | 12 | 1 | 0.01 |
| 1.04 (40% Glycerol) | 2.2 | 123 | 0.4 | 22.5 | 100 | 8 | 15 | 0.12 |

Bromophenol Blue 1.4 mM (pKa = 4.1, D = 2.71 * $10^{-10}$)

| | Experimental | | Theoretical | | | | Error | |
|---|---|---|---|---|---|---|---|---|
| HCL pH | C | Exp. width (µm) | PH change | Conc. change (%) | Theo. width (µm) | Indicator diffusion (µm) | Absolute | Relative |
| 0.086 | 4.4 | 247 | 2 | 82 | 231 | 14 | 2 | 0.01 |
| | | | 1 | 50 | 242 | 14 | −9 | −0.04 |
| | | | 0.6 | 33 | 257 | 14 | −24 | −0.10 |
| 1.08 | 3.4 | 191 | 2 | 82 | 171 | 14 | 6 | 0.03 |
| | | | 1 | 50 | 186 | 14 | −9 | −0.05 |
| | | | 0.6 | 33 | 199 | 14 | −22 | −0.12 |
| 1.9 | 2 | 112 | 2 | 82 | 105 | 14 | −7 | −0.06 |
| | | | 1 | 50 | 126 | 14 | −28 | −0.25 |
| | | | 0.6 | 33 | 144 | 14 | −46 | −0.41 |

In Table 1 above, C is a constant from the fit of $\sqrt{Dt \cdot C}$ to the experimental measured diffusion widths, "Exp. width" is the diffusion width of protons into the indicator fluid obtained from the experimental data at the time 0.3 sec. (corresponding to the time it takes to transport a molecule through a BIAcore™ flow cell at a flow rate of 10 µl/min) and "pH change" in the theoretical part is the required pH change during an ocular inspection of the indicator fluid. In the BB part the theoretical diffusion width is calculated for three different pH changes because the color change of the BB was difficult to estimate. The column "conc. change" is the corresponding concentration change to the estimated pH change (i.e., how many indicator molecules that have to be proteolysed before a color change could be seen), and "theo width" is the theoretical diffusion width calculated from the required concentration change for a color change of the indicator. The diffusion of the indicator into the acid fluid is calculated in the column "Indicator diffusion."

The pH for PR was adjusted 1.0 pH units below pKa for PR, while the pH for BB was adjusted 0.1 pH units below the pKa. Therefore, the required concentration change for a color change is larger for BB than for PR. The difference in adjusting the pH for the indicators arises from the difficulties to distinguish between the blue, blue-green-yellow and the yellow color for BB. The estimation that 0.6 pH units is enough for a color change of BB may not be accurate, and more probable is that the required concentration change was between 1 and 2 pH units. The results in Table 1 show that the derived theory may be used to predict the diffusion in the thin layer flow cell. Further, the tests with phenol red show that it is possible to calculate the diffusion in more viscose media like glycerol with desirable precision.

Figure 18:
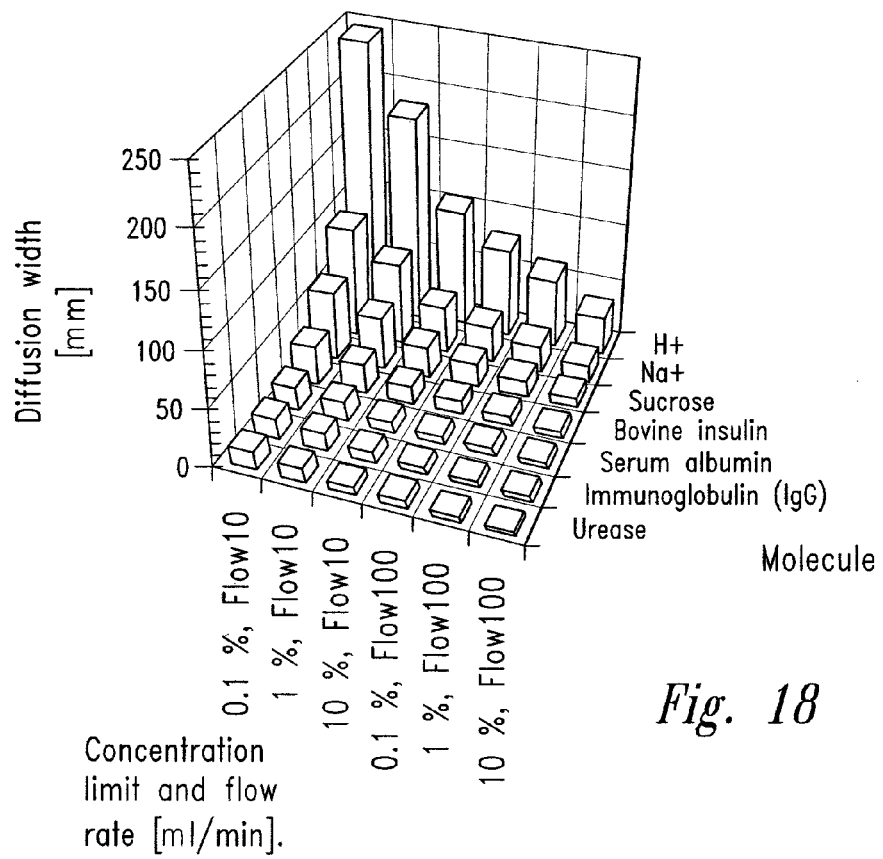
FIG. 18 graphs diffusion widths of different proteins and molecules at different flow rates and at different concentration limits.
Figure 19:
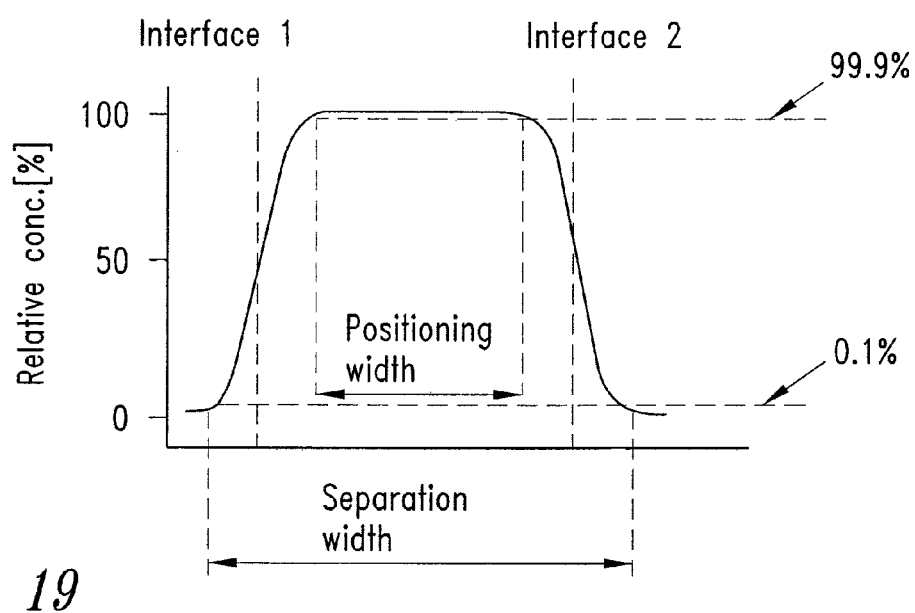
FIG. 19 is a schematic cross section of a Ψ cell with the relative sample concentration on the y-axis and length on the x-axis, perpendicular to the flow direction (the positioning width is the width where the sample concentration is >99.9%, and the separation width is where the sample concentration is <0.1%).
Figure 20A:
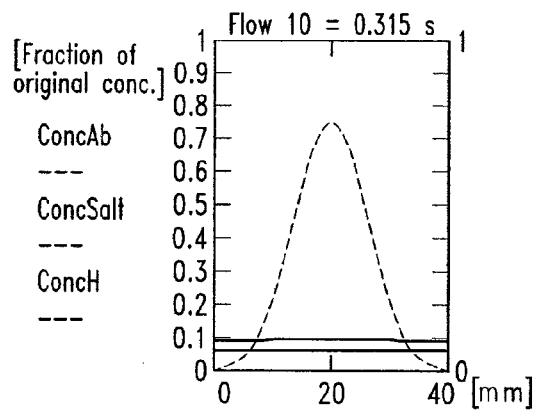
FIGS. 20A, 20B, 20C and 20D illustrate use of a Ψ flow cell for dialysis.
Figure 20B:
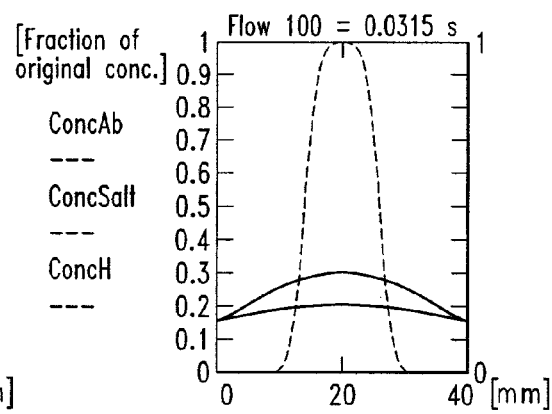
Figure 20C:
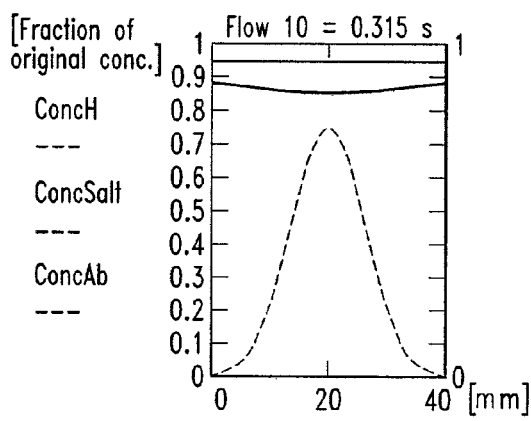
Figure 20D:
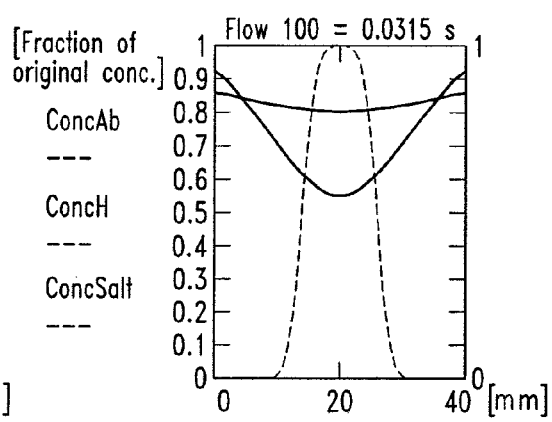

To this end, FIG. 18 shows the calculated diffusion width for some proteins of various size, as well as some small molecules, while Table 2 gives the calculated diffusion width in numbers. Further, Table 2 provides the information that is needed to calculate how many narrow bands of immobilized molecules that can be placed on the sensing surface within the flow cell. Looking at IgG, for example, at a flow rate of 100 µl/min and a separation of 0.1%, the diffusion width between the interface and 0.1% is 5 µm and the width between the interface and 99.9% is also 5 µm. If 99.9% of the original concentration is needed for detection in a band with a width of 10 µm, then the separation width is 30 µm (see FIG. 19). 30 µm narrow bands in flow cells having a width of 500 µm gives 16 possible bands in the flow cell. The same calculation for sucrose gives 10 bands in the flow cell. It should be noted, however, that the number of bands can be increased be employing a shorter sensing area, which will result in a decrease in the diffusion width, and thus an increase in the number of potential bands within the flow cell.

TABLE 2

Diffusion Width (μm) for Some Proteins and Small Molecules

|  |  |  | Flow 10 (μl/min) | | | Flow 100 (μl/min) | | |
| --- | --- | --- | --- | --- | --- | --- | --- | --- |
| Protein/Molecule | Mw | D ([m$^2$/s]) | 0.1% | 1% | 10% | 0.1% | 1% | 10% |
| Urease | 490,000 | 3.40E−11 | 14 | 11 | 6 | 5 | 3 | 2 |
| Immunoglobulin (IgG) | 156,000 | 4.00E−11 | 15 | 12 | 6 | 5 | 4 | 2 |
| Serum albumin | 64,000 | 6.15E−11 | 19 | 15 | 8 | 6 | 5 | 3 |
| Bovine insulin | 12,000 | 1.50E−10 | 30 | 23 | 13 | 10 | 7 | 4 |
| Sucrose | 337 | 5.20E−10 | 56 | 42 | 24 | 18 | 13 | 8 |
| Na$^+$ | 11 | 1.33E−09 | 90 | 68 | 38 | 28 | 21 | 12 |
| H$^+$ | 1 | 9.31E−09 | 240 | 180 | 100 | 75 | 57 | 31 |

Example 3

Ion Exchange/On-Line Dialysis

The FIG. 20 shows how an ion exchange or an on-line dialysis may be performed employing the techniques of this invention. FIGS. 20A and 20B illustrate ion exchange with low ion concentration in the adjacent buffer. FIGS. 20C and 20D demonstrate ion exchange when the ion concentration in the adjacent buffer is high. The panels shown in FIG. 20 are for two different flow rates: 10 μl/min in FIGS. 20A and 20C, and 100 μl/min in FIGS. 20B and 20D. The distance between the two interfaces is 12 μm in 20A, 20B, 20C and 20D. Referring to FIG. 20A, the flow rate is 10 μl/min and the concentration of salt and protons for the adjacent buffer is low. The salt concentration in the sample flow decreases to 10% and the proton concentration decreases to 6% of the original concentration. In FIG. 20B the flow rate is 100 μl/min, the salt concentration in the sample flow decreases to approximately 30% of the original concentration, and the proton concentration decrease to approximately 20% of the original concentration in the sample. In FIGS. 20C and 20D the adjacent buffer has a high concentration of salt and protons.

Example 4

Exchange Rates for Representative Flow Cells

A sucrose solution (5% by weight) was used to measure the liquid exchange rate in the representative Y flow cell of Example 1 (see FIG. 15), and compared with a flow cell of a commercially available BIAcore 2000 (referred to as an "IFC 3 flow cell") and from a commercially available BIAcore 1000 (referred to as an "IFC 4 flowcell"). The IFC 3 and IFC 4 flow cells are both 60 nl in volume, but different with respect to the channels that lead to the flow cells and to placement of the valves. In this experiment, reference to the IFC 3 and IFC 4 flow cells include the channels, valves and 60 nl flow cells.

The rise time was measured as the time it takes to reach 99% of the plateau value for different flow rates through the tested flow cells. Plotting the rise time against the flow rate, and fitting this curve with Equation (9) gives a constant $V_a$. With this constant it is possible to calculate both the liquid exchange rate for different flow rates and the liquid exchange rate constant for the flow cell.

A fast liquid exchange during the rise in the Y flow cell was accomplished as follows. Before the sample was introduced into the flow cell only buffer was running through the flow cell. The sample flow valves shifted and the sample entered the flow cell. The sample flow filled up only a narrow part of the flow cell. At the liquid exchange, the valve to the buffer flow closed and the sample flow displaced the buffer and filled up the flow cell. The fall was done in the same way as the rise. The buffer entered the flow cell and filled up only a narrow part of the flow cell. The sample flow valve closed and the buffer flow displaced the sample fluid. The time it took to cover up the sensing area corresponded to the movement of the interface over the sensing area and the dispersion of the interface. In this context, the sensing area was an approximately 1.6 mm by 0.17 mm area located between inlet 2 and outlet 2 of FIG. 15 (with the total sensing surface being roughly 2.4 mm by 0.8 mm).

Figure 21A:
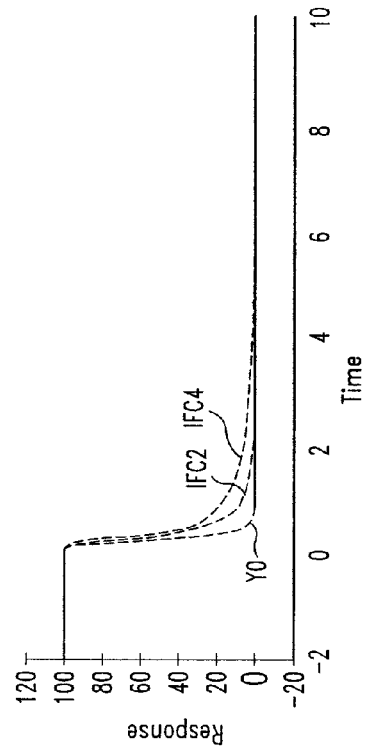
FIGS. 21A and 21B represent the part of the sensorgrams that show the rise and fall times, respectively, for different flow cells.
Figure 21B:
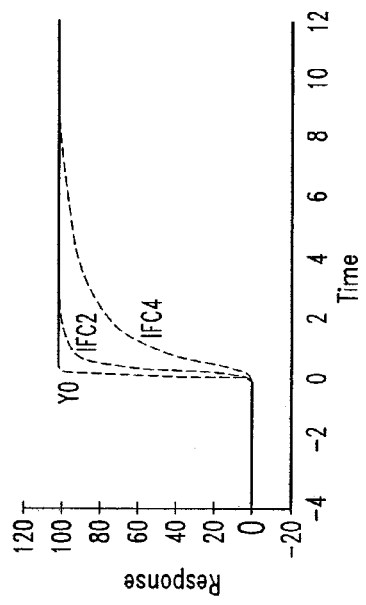
Figure 21C:
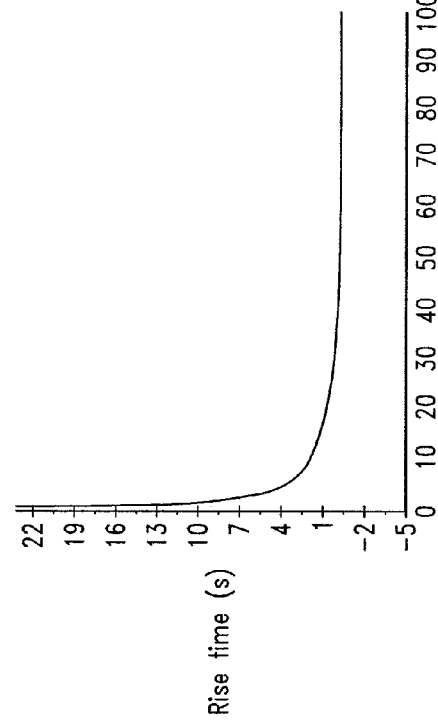
FIG. 21C shows a plot of rise time versus sample flow.

FIGS. 21A and 21B compare the sensorgrams for the Y, IFC 3 and IFC 4 flow cells. To obtain an experimental relation between the rise time and the flow rate the rise time to 99% of the steady state concentration was measured and plotted versus the sample flow (see FIG. 21C) according to Equation (9).

Figure 22:
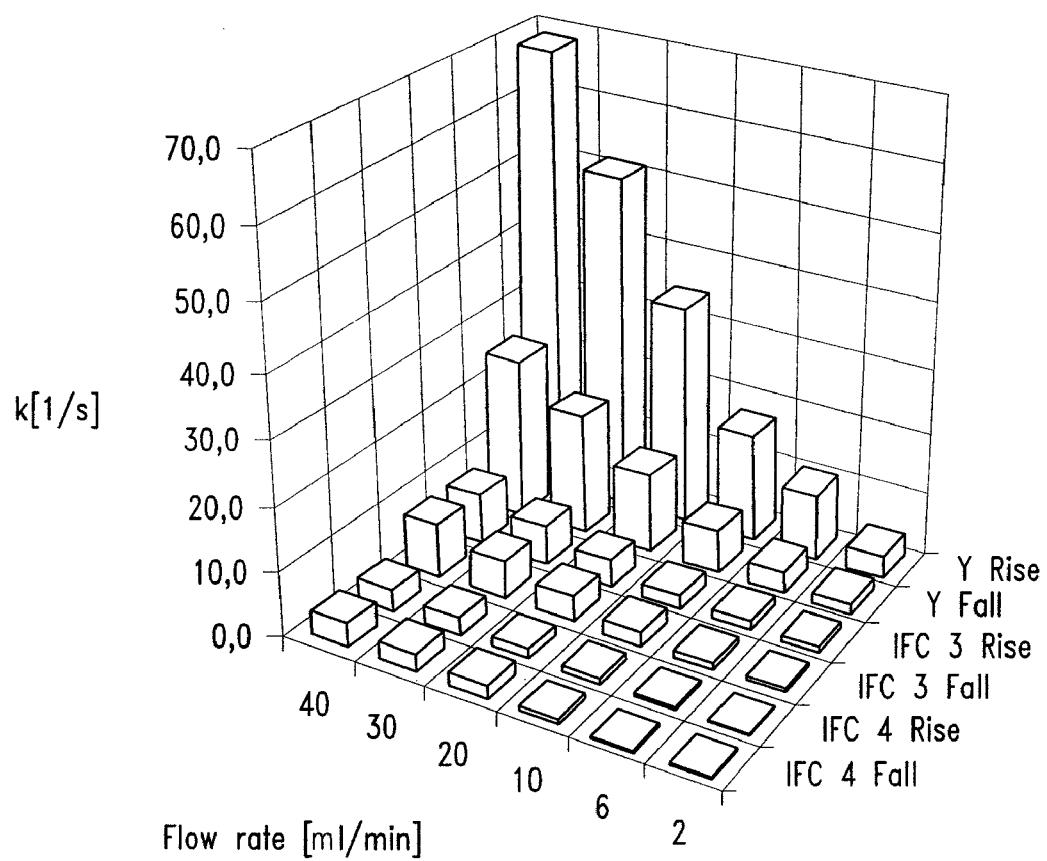
FIG. 22 presents a comparison of the liquid exchange rate constants for representative Y, IFC3 and IFC4 flow cells.

Equation (10) was used to calculate the liquid exchange rate constant for different flow rates. To get a valid estimate of the reaction rates, $K_{Lqx}$>>than the on-rate and the off-rate. The larger $K_{Lqx}$ the faster kinetics can be measured. The results of this calculation are present in FIG. 22 which shows a comparison of the liquid exchange rates for the different flow cells at different flow rates.

In the BIAcore IFC 3 and IFC 4 flow cells the interface is rinsed out over the length of the sensing area and the length of the detection area is 10 times the width. In the Y flow cell the interface is displaced over the sensing area in a direction parallel to the width of the flow cell (i.e., transverse to the side wall). Thus, the distance that the interface must travel is 10 times less than for the IFC 3 or IFC 4 flow cells. This movement transverse to the flow direction, combined with the small dispersion in the Y flow cell, explains why the exchange of fluids can be done much faster in the Y flow cell.

The faster liquid exchange during the rise for the Y flow cell than for the fall (see FIG. 22) is due to the fact that the required sample flow is lower before the rise than during the fall relative to the total flow in the flow cell. The higher flow before the fall for the Y flow cell is required to cover the sensing area (i.e., the interface is further away from the sample flow inlet). The buffer flow valve in the IFC 3 and IFC 4 flow cells is placed closer to the flow cell than the sample flow valves (i.e., the dispersion in the IFC3 and 4 flow cells is less for the liquid exchange to buffer flow than for the liquid exchange to sample flow). These two effects together explain the improvement of the rise compared to the fall.

Example 5

Sensitization and Analysis

This experiment illustrates the use of a representative Y flow cell of this invention to immobilize two different ligands on discrete sensing areas. Immobilization was done with two fluid flows passing through the flow cell side-by-side under laminar flow conditions. A BIACore 2000 was employed for this experiment, using the Y flow cell of FIG. 15. FIG. 23A shows the result of the immobilization of a first ligand (i.e., biotinylated oligonucleotide 15-mer, called "R1") over sensing area 1 and the outline of the Y flow cell during the immobilization. During the immobilization there were no responses from sensing areas 2 and 3. The sensorgram shows a bulk effect from the immobilization flow, but not from the buffer flow over sensing area 2 and 3. During the immobilization of a second ligand (i.e., a different biotinylated oligonucleotide 15-mer called "R2") over sensing area 3, there was no response from sensing areas 1 and 2, as shown by FIG. 23B. These sensorgrams clearly show that the Y flow cell is very good for immobilization of two different ligands in a single flow cell.

FIG. 23C shows the injection of an analyte (i.e., a oligo 16-mer, called "R4", complementary to R1). The entire sensing surface was contacted with the analyte. Even though the analyte was in contact with both of the sensitized areas (i.e., sensing areas 1 and 3), only the specific interaction with sensing area 1 gave a response. The non-interacting ligand and the non-sensitized area can be used as references. FIG. 23C shows a bulk effect from all the sensing areas, this bulk effect is subtracted out in FIG. 23E. FIG. 23D shows the injection of a different analyte (an oligo 16-mer complementary, called "R5", complementary to R2). The bulk effect is around 100 RU, but the bulk effect may be subtracted as shown in FIG. 23F.

From the foregoing, it will be evident that, although specific embodiments of the invention have been discussed herein for purpose of illustration, various modifications may be made without deviating from the spirit and scope of the invention.

We claim:

1. A sensor device comprising a flow cell having an inlet end and an outlet end, at least one sensing surface on a wall surface within the flow cell located between the inlet and outlet ends, wherein the sensing surface and the flow cell are turnably arranged with respect to each other to permit fluid flow over the sensing surface in a first direction and in a second direction in an angular relationship to the first direction.

2. The sensor device of claim 1, wherein the second direction is transverse to the first direction.

3. The sensor device of claim 1, wherein the flow cell has two inlet openings and at least one outlet opening.

4. The sensor device of claim 1, wherein the flow cell has three inlet openings and at least one outlet opening.

5. The sensor device of claim 1, wherein the sensing surface has at least two discrete sensing areas thereon.

6. The sensor device of claim 5, wherein one of the at least two discrete sensing areas is a reference area.

7. The sensor device of claim 5, wherein one of the at least two discrete sensing areas is capable of specifically interacting with an analyte.

8. A sensor system, comprising the sensor device of claim 1, further comprising:
means for applying fluid flow through the flow cell; and
detection means for detecting interaction events on the sensing surface.

9. The sensor system of claim 8, wherein the detection means comprises an optical sensor.

10. The sensor system of claim 9, wherein the optical sensor is based on evanescent wave sensing.

11. The sensor system of claim 9, wherein the optical sensor is an SPR-sensor.

* * * * *